US008313432B2

(12) United States Patent
Chiu et al.

(10) Patent No.: US 8,313,432 B2
(45) Date of Patent: Nov. 20, 2012

(54) SURGICAL DATA MONITORING AND DISPLAY SYSTEM

(75) Inventors: John C. Chiu, Thousand Oaks, CA (US); Han K. Huang, Agoura Hills, CA (US)

(73) Assignee: SurgMatix, Inc., Thousand Oaks, CA (US)

( * ) Notice: Subject to any disclaimer, the term of this patent is extended or adjusted under 35 U.S.C. 154(b) by 1101 days.

(21) Appl. No.: 12/143,711

(22) Filed: Jun. 20, 2008

(65) Prior Publication Data

US 2008/0319275 A1 Dec. 25, 2008

Related U.S. Application Data

(60) Provisional application No. 60/936,639, filed on Jun. 20, 2007.

(51) Int. Cl.
*A61B 5/00* (2006.01)
(52) U.S. Cl. .................. 600/300; 600/301; 705/2; 705/3
(58) Field of Classification Search .................. None
See application file for complete search history.

(56) References Cited

U.S. PATENT DOCUMENTS

| 4,817,091 | A | * | 3/1989 | Katzman et al. ............. 714/6.13 |
| 5,262,944 | A | * | 11/1993 | Weisner et al. ............... 600/300 |
| 5,331,549 | A | * | 7/1994 | Crawford, Jr. ............... 600/513 |
| 5,788,688 | A | * | 8/1998 | Bauer et al. ........................ 606/1 |
| 5,819,229 | A | * | 10/1998 | Boppe ............................... 705/2 |
| 5,848,173 | A | * | 12/1998 | Sato et al. ....................... 381/398 |
| 6,928,490 | B1 | * | 8/2005 | Bucholz et al. ............... 709/249 |
| 2002/0177758 | A1 | * | 11/2002 | Schoenberg et al. .......... 600/300 |
| 2002/0188213 | A1 | | 12/2002 | Bardy |
| 2003/0153818 | A1 | | 8/2003 | Bocionek et al. |
| 2003/0156745 | A1 | * | 8/2003 | Saito et al. ..................... 382/128 |
| 2004/0059604 | A1 | * | 3/2004 | Zaleski ............................. 705/2 |
| 2005/0038326 | A1 | | 2/2005 | Mathur |
| 2005/0101844 | A1 | | 5/2005 | Duckert et al. |
| 2005/0149363 | A1 | * | 7/2005 | Loiterman et al. ............... 705/3 |
| 2006/0085299 | A1 | * | 4/2006 | Goll et al. ........................ 705/28 |
| 2006/0206011 | A1 | * | 9/2006 | Higgins et al. ............... 600/300 |
| 2006/0226308 | A1 | * | 10/2006 | White et al. ............... 248/122.1 |
| 2007/0168461 | A1 | * | 7/2007 | Moore .......................... 709/217 |
| 2007/0260126 | A1 | * | 11/2007 | Haumann et al. ............. 600/300 |

* cited by examiner

*Primary Examiner* — Henry M. Johnson, III
*Assistant Examiner* — Marie Archer
(74) *Attorney, Agent, or Firm* — James W. Hill; McDermott Will & Emery LLP

(57) ABSTRACT

A surgical data monitoring and display system is described. In some embodiments, the system includes a data storage module that stores retrospective data and real-time surgical data concerning a patient, a first processing module that receives and processes the retrospective data into processed retrospective data, and a second processing module that receives and processes the real-time data into processed real-time data. Each of the first processing module and the second processing module transmits their processed data to first and second display modules, respectively, before or during performance by a healthcare provider of a medical or surgical procedure on the patient.

32 Claims, 19 Drawing Sheets

FIG. 4B

SURGICAL DATA MONITORING AND DISPLAY SYSTEM

PRIORITY CLAIM

This application claims the benefit of U.S. Provisional Application Ser. No. 60/936,639, filed on Jun. 20, 2007, and titled "SURGICAL DATA MONITORING AND DISPLAY SYSTEM," the entirety of which is hereby incorporated by reference.

BACKGROUND OF THE INVENTION

1. Field of the Invention

Embodiments of the invention relate to information display systems. More specifically, some embodiments of the invention relate to a multidisplay system for operating rooms or medical procedure rooms.

2. Description of the Related Art

Surgeons need to know various items of information concerning a patient before, during, and after surgery, but this information is often delivered asynchronously, incompletely, or in an otherwise non-centralized, piecemeal, or delayed fashion.

SUMMARY OF THE INVENTION

It is important in an operating room setting for a surgeon to have access to many different types of patient information. For example, a surgeon may need preoperative information (i.e., information available before surgery or "retrospective" information), such as a patient's identification, medical history, prior imaging or laboratory studies, and three dimensional (3-D) magnetic resonance (MR) or computed tomography (CT) rendering, and a surgical plan. A surgeon may also need intraoperative information (i.e., information during a surgery or "real-time" information), such as vital signs, fluid intake and output electrocardiographic data, neurophysiological data (e.g., somatic sensory evoked potentials (SSEP) data), electroencephalographic data, electromyogram data, pulse oximetry data, digital C-arm fluorographic images, endoscopic video images, additional verification medical images, and live surgical video images. In some cases, a surgeon may want to verify information intraoperatively, such as a patient's biometric information for patient verification. In some instances, the surgeon may postoperatively (i.e., after surgery) review both the preoperative and intraoperative information in order to document in the patient's record the surgical procedure performed, the patient's immediate postoperative condition, and the surgical outcome.

In many cases, some or all of the preoperative, intraoperative, or postoperative information may not be easily accessible by the surgeon. In some cases, if some of this information is available in the operating room, it may be presented on multiple displays or through other output devices inaccessible to the surgeon from any one location. In these cases, the surgeon may have to rely on others in order to obtain the information, which could be problematic in a time-critical environment.

Consequently, a system is needed for making intraoperative data (e.g., real-time surgical and/or medical data), preoperative data (i.e., retrospective or historical patient data), and postoperative data immediately accessible to a surgeon or other healthcare practitioner in a patient care area.

In certain embodiments, a surgical data monitoring and display system for use in an operating room or another patient care room is disclosed. The system includes a data storage module that stores retrospective data and real-time surgical data concerning a patient, and a first processing module that receives the retrospective data, processes the retrospective data into processed retrospective data, and transmits the processed retrospective data to a first display module before or during performance of a medical or surgical procedure on the patient by a healthcare provider. The system also includes the first display module, which displays the processed retrospective data, a first gateway that receives the retrospective data from a server and transmits the retrospective data to the data storage module, and a second processing module that receives the real-time data, processes the real-time data into processed real-time data, and transmits the processed real-time data to a second display module before or during performance of the medical or surgical procedure on the patient by the healthcare provider. The system further includes the second display module, which displays the processed real-time data. The real-time data concerning the patient includes at least two of the following: electrocardiographic data, electroencephalographic data, pulse oximetry data, videoscopic data, and vital sign data. The retrospective data includes at least one of imaging data, patient identification information, past medical history information, physical examination information, data concerning a past procedure performed on the patient, and data concerning another patient or a teaching case. The real-time data is acquired during performance of the medical or surgical procedure on the patient. The first display module and the second display module are positionable in the operating room or another patient care room such that they are viewable by the healthcare provider during the performance by the healthcare provider of the medical or surgical procedure on the patient. The system yet further includes a third processing module configured to receive postoperative data, the retrospective data, and the real-time data, and further configured to process at least one of the postoperative data, the retrospective data, and the real-time data into report data, and a third display module, which displays the report data.

In certain embodiments, the system includes an alert module, coupled to the second processing module and configured to provide a visible alert when a predetermined threshold of the real-time data is exceeded. The visible alert includes at least one of moving displayed real-time data from a first location, less prominent on a display of the second display module to the healthcare provider, to a second location, more prominent on the display of the second display module to the healthcare provider, and enlarging a display, of first set of the processed real-time data, displayed at a first, smaller size on a display of the second display module, to a second, larger size on the display of the second display module. The first set of the processed real-time data includes at least one of electrocardiographic data, electroencephalographic data, pulse oximetry data, videoscopic data, and vital sign data. The display of the second display module further displays a second set of the processed real-time data adjacent to the display of the first set of the processed real-time data, the second set of the processed real-time data includes at least one of electrocardiographic data, electroencephalographic data, pulse oximetry data, videoscopic data, and vital sign data. When the display of the first set of the processed real-time data is enlarged to the second, larger size on the display of the second display module, the display of the first set of the processed real-time data (i) overlaps the display of the second set of the processed real-time data, and/or (ii) the display of the second set of the processed real-time data is reduced in size.

In certain embodiments, the visible alert further includes changing a color of displayed real-time data on a display of the second display module. In certain embodiments, the system includes alert module, coupled to the second processing module and configured to provide a visible alert when a predetermined threshold of the real-time data is exceeded. The visible alert includes changing a color of displayed real-time data on a display of the second display module. In certain embodiments, the first gateway is configured to receive and transmit the retrospective data according to a predefined priority configuration. In certain embodiments, the first processing module and the second processing module comprise the same hardware or software processor. In certain embodiments, at least two of the first processing module, the second processing module, and third processing module provide fault tolerance for each other. In certain embodiments, the system includes a fourth display module configured to provide fault tolerance for each of the first display module, the second display module, and third display module. In certain embodiments, the report data includes a patient surgery record. In certain embodiments, the vital sign data includes at least one of a heart rate, a respiratory rate, a blood pressure, and a body temperature. In certain embodiments, the system includes a second gateway that receives the real-time data from a server and transmits the real-time data to the data storage module, and a third gateway that receives the postoperative data and transmits the postoperative data to the data storage module. In certain embodiments, each of the first gateway, the second gateway, and the third gateway provide fault tolerance for each other. In certain embodiments, the first gateway, the second gateway, and the third gateway constitute the same node on a computer network. In certain embodiments, the system includes an imaging server, the first processing module receives the retrospective data from the imaging server, and the retrospective data includes imaging data. In certain embodiments, the imaging server includes a picture archiving and communications system (PACS) server. In certain embodiments, the real-time data further includes at least one of electromyogram (EMG) data, imaging data, computed tomography (CT), magnetic resonance image (MRI) data, ultrasound data, C-Arm image data, fluoroscopy data, and X-Ray data.

In certain embodiments, a surgical data monitoring and display system for use in an operating room or another patient care room is disclosed. The system includes a data storage module that stores real-time surgical data concerning a patient, a first processing module that receives the real-time data, processes the real-time data into processed real-time data, and transmits the processed real-time data to a first display module before or during performance of a medical or surgical procedure on the patient by the healthcare provider, and the first display module, which displays the processed real-time data. The real-time data concerning the patient includes at least two of the following: electrocardiographic data, electroencephalographic data, pulse oximetry data, videoscopic data, and vital sign data. The real-time data is acquired during performance of the medical or surgical procedure on the patient. The first display module is positionable in the operating room or another patient care room such that they are viewable by the healthcare provider during the performance by the healthcare provider of the medical or surgical procedure on the patient. The system also includes a second processing module configured to receive postoperative data, retrospective data, and the real-time data, and further configured to process at least one of the postoperative data, the retrospective data, and the real-time data into report data, a second display module, which displays the report data, and an alert module, coupled to the first processing module and configured to provide a visible alert when a predetermined threshold of the real-time data is exceeded. The visible alert includes at least one of moving displayed real-time data from a first location, less prominent on a display of the first display module to the healthcare provider, to a second location, more prominent on the display of the first display module to the healthcare provider, and enlarging a display of first set of the processed real-time data, displayed at a first, smaller size on a display of the first display module, to a second, larger size on the display of the first display module. The first set of the processed real-time data includes at least one of electrocardiographic data, electroencephalographic data, pulse oximetry data, videoscopic data, and vital sign data. The display of the first display module further displays a second set of the processed real-time data adjacent to the display of the first set of the processed real-time data, the second set of the processed real-time data includes at least one of electrocardiographic data, electroencephalographic data, pulse oximetry data, videoscopic data, and vital sign data. When the display of the first set of the processed real-time data is enlarged to the second, larger size on the display of the first display module, the display of the first set of the processed real-time data (i) overlaps the display of the second set of the processed real-time data, and/or (ii) the display of the second set of the processed real-time data is reduced in size.

In certain embodiments, the system includes a third processing module that receives the retrospective data, processes the retrospective data into processed retrospective data, and transmits the processed retrospective data to a third display module before or during performance of the medical or surgical procedure on the patient by the healthcare provider, the third display module, which displays the processed retrospective data, and a third gateway that receives the retrospective data from a server and transmits the retrospective data to the data storage module. In certain embodiments, the third gateway is configured to receive and transmit the retrospective data according to a predefined priority configuration. In certain embodiments, the first processing module, the second processing module, and the third processing module comprise the same hardware or software processor. In certain embodiments, at least two of the first processing module, the second processing module, and third processing module provide fault tolerance for each other. In certain embodiments, the system includes a fourth display module configured to provide fault tolerance for each of the first display module, the second display module, and third display module. In certain embodiments, the report data includes a patient surgery record. In certain embodiments, the vital sign data includes at least one of a heart rate, a respiratory rate, a blood pressure, and a body temperature. In certain embodiments, the system includes a second gateway that receives the postoperative data and transmits the postoperative data to the data storage module, and a third gateway that receives the real-time data from a server and transmits the real-time data to the data storage module. In certain embodiments, each of the first gateway, the second gateway, and the third gateway provide fault tolerance for each other. In certain embodiments, the first gateway, the second gateway, and the third gateway constitute the same node on a computer network. In certain embodiments, the system includes an imaging server, the third processing module receives the retrospective data from the imaging server, and the retrospective data includes imaging data. In certain embodiments, the imaging server includes a picture archiving and communications system (PACS) server. In certain embodiments, the real-time data further includes at least one of electromyogram (EMG) data, imaging data, computed tomography (CT), magnetic resonance image (MRI) data, ultrasound data, C-Arm image data, fluoroscopy data, and X-Ray data.

For purposes of summarizing the invention, certain aspects, advantages, and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 4B illustrates a sample screenshot from a preoperative data display according to one embodiment of the invention.

DETAILED DESCRIPTION OF EXEMPLARY EMBODIMENTS

Figure 1:
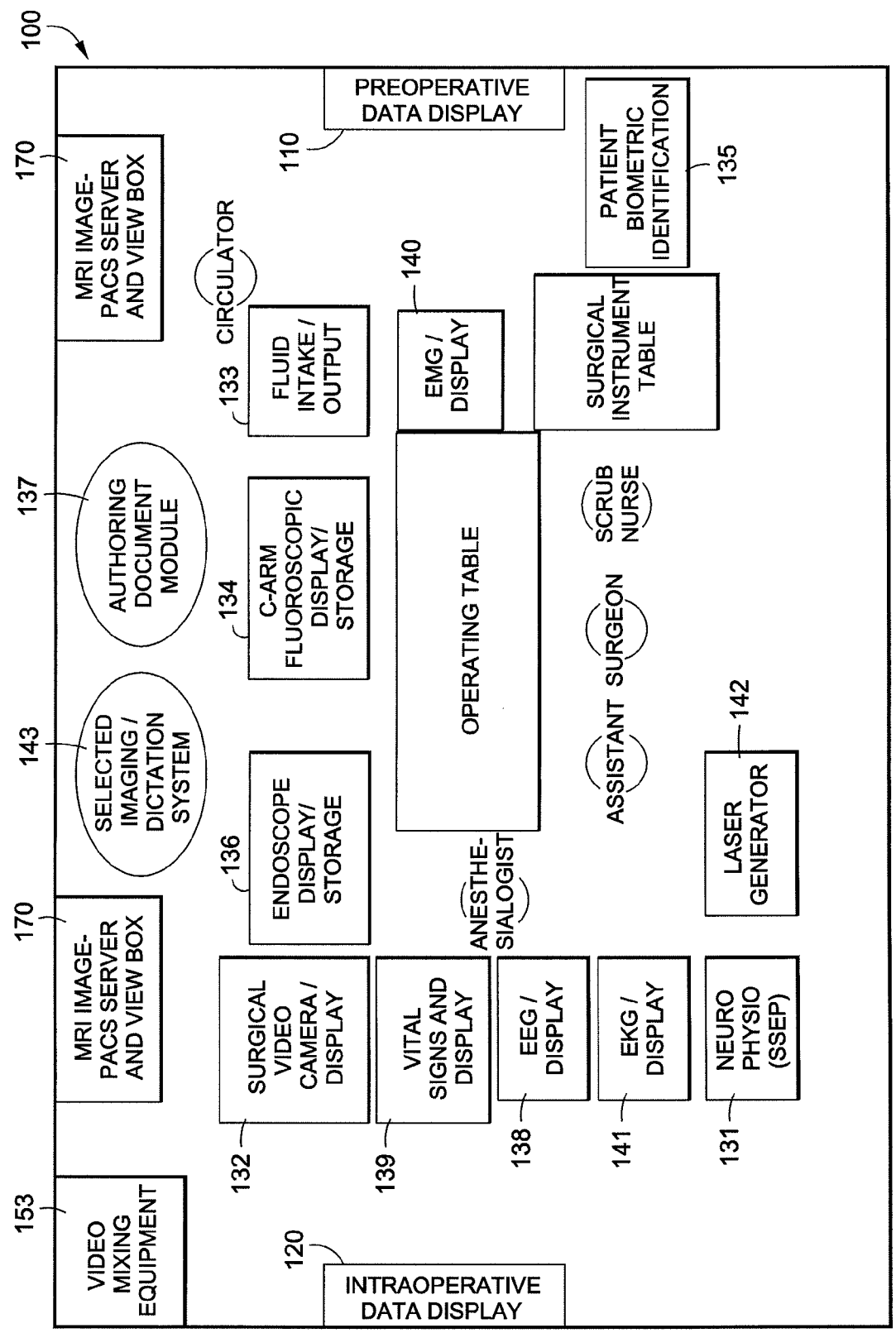
FIG. 1 illustrates an operating room layout which includes a surgical data monitoring and display system according to one embodiment of the invention.

FIG. 1 illustrates an operating room layout 100 which includes a surgical data monitoring and display system according to one embodiment of the invention. As used herein, the term "data" includes, without limitation, textual data, waveform data and image data. The surgical data monitoring and display system can obtain and display intraoperative (real-time medical or surgical) data and preoperative data from many different sources. As used herein, the term "preoperative data" and "intraoperative data" includes, without limitation, surgical, medical, physiological, or psychiatric information that is preoperative, intraoperative, postoperative, or surgical in nature. The illustrated operating room layout 100 includes a plurality of data sources and devices, including video mixing equipment 153, a magnetic resonance image (MRI) Picture Archive and Communication System (PACS) server and view box 170, an imaging/dictation system 143, an authoring document module 137, a surgical video camera/display 132, an endoscope display/storage 136, a C-arm fluoroscopic display/storage 134, a fluid intake/output 133, a vital sign display 139, an electromyogram (EMG) display 140, an electroencephalograms (EEG) display 138, a patient biometric identifier 135, a neuro-physiological monitor 131, an electrocardiogram (EKG) display 141, a laser generator 142, an intraoperative data display 120, and a preoperative data display 110.

In certain embodiments, the laser generator 142 is modified to record input voltage, ampere, and output laser energy. The recorded output laser energy can dictate the level of laser power delivered to a patient, and that information can allow a surgeon to monitor the amount of cutting and healing of tissues, such as by viewing the energy level on the intraoperative display 120 during surgery.

In certain embodiments, the surgical video camera/display 132 and video-mixing equipment 153 are configured to create another recording for postoperative use by using either the historical data or the real-time data. Sample postoperative uses include documentation or use as an instructive student training video.

The surgical data monitoring and display system comprises the integration of image and data information sources, including preoperative data, intraoperative data, and postoperative data. Preoperative data can include, for example, image information such as images from radiography, including myelograms, fluoroscopy 134, MRI 170, X-ray tomograms, computed tomography (CT) 170, and/or ultrasound (US). Preoperative data can also include, for example, information concerning other patients and/or teaching cases, procedures, surgical protocol, instruction manuals, patient history data, evaluation data, identification data, biometric data, scanned data (which may be stored as PDF files), and previously recorded intraoperative data.

Intraoperative data can include, for example, real-time information from various sources used during surgery, such as surgical video 132, C-ARM fluoroscopy 134, endoscopic images 136, and waveform signals, such as from EEG 138, EMG 140, EKG 141, vital signs 139, neuro-physiological monitors 131 (e.g., monitoring somatic sensory evoked potentials (SSEP) data), fluid intake and output 133, and patient biometric identification 135. Postoperative data can include, for example, authored, dictation, and/or imaging information received from the selected imaging/dictation system 143, surgical procedure reports, postoperative graphical user interface data, data received in a recovery room, such as from input devices similar to the intraoperative devices discussed above, sensor input from a telemetry device, data entered manually after the completion of the surgical procedure, or any other data received after the completion of the surgical procedure.

In certain embodiments, the intraoperative data and preoperative data are displayed on a plurality of displays. In the illustrated embodiment, two displays, preoperative data display 110 and intraoperative data display 120, are used. In certain embodiments, one display can be used. Any display technology can be used, including, but not limited to, plasma displays, liquid crystal displays (LCD), nanocrystal displays, three-dimensional (3D) displays, cathode ray tube (CRT) displays, light emitting diode (LED) displays, nano-emissive displays, and projection displays. In certain embodiments, preoperative data and/or intraoperative data is selected for display by interacting with the electronic patient record (ePR) server 221, described further below with reference to FIG. 2.

In certain embodiments, the surgical data monitoring and display system is configured to connect to the preoperative, intraoperative, and postoperative data sources discussed above. In certain embodiments, the intraoperative data sources need to be synchronized against a master clock because the real-time information, such as text, waveform data and images, generated from intraoperative data sources can each have its own independent clock cycle synchronized against its own independent internal clock.

With regards to intraoperative data sources that produce waveform data (e.g., EEG 138, vital signs 139, EMG 140, EKG 141, output from a laser generator 142, and pressure waves and values from transducers associated with intravascular or intracardiac catheters, such as a Swan-Ganz catheter), the internal clock each data source is converted to a master clock so that each data source is synchronized. The master clock is used to trigger the interaction of each of the devices. The internal clocks may thus be converted to an acceptable rate favorable to a surgical procedure so that data input to an input gateway (e.g., input gateway 210 in FIG. 2, discussed in further detail below) is acquired according to a preset time unit, and controlled by a single master clock. Similarly, the display of each of the intraoperative data sources that produce waveform data is sampled to display data at the proper coordinates of the intraoperative display 120 at the appropriate time according to the master clock.

In certain embodiments, the surgical data monitoring and display system obtains preoperative data from an information archive, such as a data server. In the illustrated embodiment, preoperative data is retrieved from storage at least in part on a PACS image server 170. In certain embodiments, the surgical data monitoring and display system obtains intraoperative data from intraoperative surgical sources, as discussed above. Because of the large amount of data that can potentially be received from these sources, and because of the need to archive and display the data, the surgical data monitoring and display system advantageously converts received data to compatible formats using an advantageous combination of industrial standards and innovative high speed communication protocols, such as the Digital Imaging and Communication in Medicine (DICOM) standard.

In certain embodiments, image data produced and received from intraoperative data sources (e.g., C-ARM fluoroscopy 134, endoscope 136, and/or others, depending on the necessity of imaging-guided requirements during the surgery) may not conform to the DICOM standard in its original form. Consequently, in certain embodiments, the intraoperative image data is conformed to the DICOM standard during a high rate image data acquisition process. The data acquisition rate may be synchronized against the same master clock used to synchronize the intraoperative waveform data.

In certain embodiments, it may take at least three times longer to acquire intraoperative image data as compared to a sample of intraoperative waveform data, consequently, clinical experience of a physician may be used to determine how to synchronize each of the intraoperative image data and intraoperative waveform data to the master clock so that the intraoperative image data and intraoperative waveform data are displayed according to a surgically acceptable time scale.

Intraoperative image data may be annotated during surgery to pinpoint a location of a lesion, such as for image-guided surgery. In certain embodiments, annotations may be added on image data while the image data is being acquired, and later archived the image data with the annotations. Furthermore, images may selectively be displayed on the intraoperative display 120 with or without annotations. Allocation of proper real estate on the intraoperative display 120 along with sampled waveform data in real-time with continuous data acquisition is advantageously achieved. The feature allowing annotations to be added on image data while the image data is being acquired may advantageously be used with the DICOM Structured Reports standard, which uses pointers to store and retrieve pertinent waveform data and images along with annotation overlay.

FIG. 2A illustrates a data workflow 200 of the surgical data monitoring and display system according to one embodiment of the invention. The input gateway 210 includes three input gateways: preoperative input gateway 211 (e.g., a first sub-gateway for retrospective data), intraoperative input gateway 242 (e.g., a second sub-gateway for real-time data), and postoperative input gateway 243 (e.g., a third sub-gateway for post-surgical data). In certain embodiments, preoperative input gateway 211 receives and processes preoperative data 201 before a surgical procedure begins that may use the preoperative data. The intraoperative input gateway 242 receives and processes intraoperative data 241. The postoperative input gateway 243 receives and processes postoperative data 244. In certain embodiments, each of the preoperative input gateway 211, intraoperative input gateway 242, and postoperative gateway 243 has its own designated priority of receiving and processing preoperative, intraoperative, and postoperative data respectively.

The postoperative input gateway 243 is configured to provide selected postoperative data to ePR module 220, and incorporate preoperative and postoperative data, such as questionnaires. The postoperative input gateway 243 is also configured to conform postoperative data to standards (e.g., image and data standards) used for data processed through the preoperative input gateway 211 and intraoperative input gateway 242. The postoperative input gateway 243 is yet further configured to organize any combination of a patient's preoperative data, intraoperative data, and postoperative data into the ePR module 220.

In certain embodiments, input gateway 210 provides fault tolerance. In certain other embodiments, the input gateway 210 does not provide fault tolerance. In certain embodiments, the fault-tolerance of the input gateway 210 has the ability to automatically use either of the preoperative input gateway 211, intraoperative input gateway 242, or postoperative input gateway 243 to receive both preoperative, intraoperative, and postoperative data should any of the other input gateways fail.

In addition to retrieving and transmitting data, the input gateway 210 is configured to act as a portal for converting and/or connecting multiple network connections which may use different standards and/or protocols, such as an interface between a World Wide Web or intranet server and an information source. The input gateway 210 can also act as a router configured to receive input from multiple sources, including the Internet. The input gateway 210 advantageously features methods to assure the fault tolerance of each of the two input gateways 211, 342, as discussed above. The input gateway 210 also advantageously features software and/or hardware to convert data and communications in non-industry-standard formats to industry-standard formats In certain embodiments, preoperative data 201 is transmitted from the preoperative input gateway 211 of the input gateway 210 to the ePR module 220. Similarly, in certain embodiments, after intraoperative data 341 has been transmitted to the intraoperative gateway 342 of the input gateway 210, the input gateway 210 processes the intraoperative data 341, and transmits the processed intraoperative data 341 to the ePR module 220. The ePR module 220 further processes the intraoperative data, and transmits the intraoperative data to the visualization and display module 330 so that the intraoperative data can be displayed 122.

In certain embodiments, the ePR module 220 comprises an ePR server 321, a monitoring module 322, and an archive/database 323 (i.e., a data storage module). In certain embodiments, the ePR module 220 comprises a processing module that processes the historical data. The ePR server 221 supervises data received from the input gateway 210, and distributes data to the visualization and display module 330. The monitoring module 222 sorts and directs multiple inputs to the ePR module 220 and distributes multi-faceted output data. The archive/database module 223 stores data.

The ePR module 220 processes the historical data and sends the processed historical data to the visualization and display module 330 so that the processed historical data can be displayed 112.

In the illustrated embodiment, the ePR module 220 provides fault tolerance. In certain other embodiments, the ePR module 220 does not provide fault tolerance. The ePR module 220 has built-in fault-tolerance for any of its three components: ePR server 321, monitoring module 322, and archive/database 323. Replication, redundancy, and/or diversity of components and data storage can be used to provide fault-tolerance if a component of the ePR module 220 fails during operation.

Fault tolerance provides multiple levels of backup in each component, such as for the interface units for each of preoperative data 201, intraoperative data 241, and postoperative data 244, input gateway 210, which includes preoperative input gateway 211, intraoperative input gateway 242, and postoperative input gateway 243, ePR module 220 and its components, ePR server 221, monitoring module 222, and archive/database 223; and visualization and display module 230 and its components, preoperative data display 110, intra-operative data display 120, and postoperative data display 130.

In certain embodiments, there are two fault-tolerant resources, software and hardware. The types of software include (1) function software configured to perform special functions specified in the completed system, (2) operation software which directs, monitors and supports the function software, and (3) fault-tolerant software. Function software, such as software for input gateway functions, query/retrieve data functions, archived functions, and display functions is configured for a clinical environment. Operation software may use off-the-shelf computer operating systems and commercially available databases. Fault-tolerant software is also configured for clinical evaluation.

The second fault-tolerant resource is hardware. In certain embodiments, if a hardware failure occurs, the fault-tolerant software will perform three steps to recover the failure (1) the fault-tolerant software detects the hardware failure and automatically shifts the operation to backup hardware, (2) the system operator can manually replace the failed hardware, and (3) the fault-tolerant software can then detect that the failed hardware has been replaced, and shift back to normal operation using the replaced hardware. The hardware fault tolerance used in this system is based at least in part on the concept of Triple Modular Redundancy (TMR). The TMR concept may be applied across the surgical data workflow described in FIG. 2, beginning with when the input gateway 210 receives any input data from a intraoperative device until that input data is successfully archived in the ePR module 220 and displayed using the visualization and display module 230.

Figure 2:
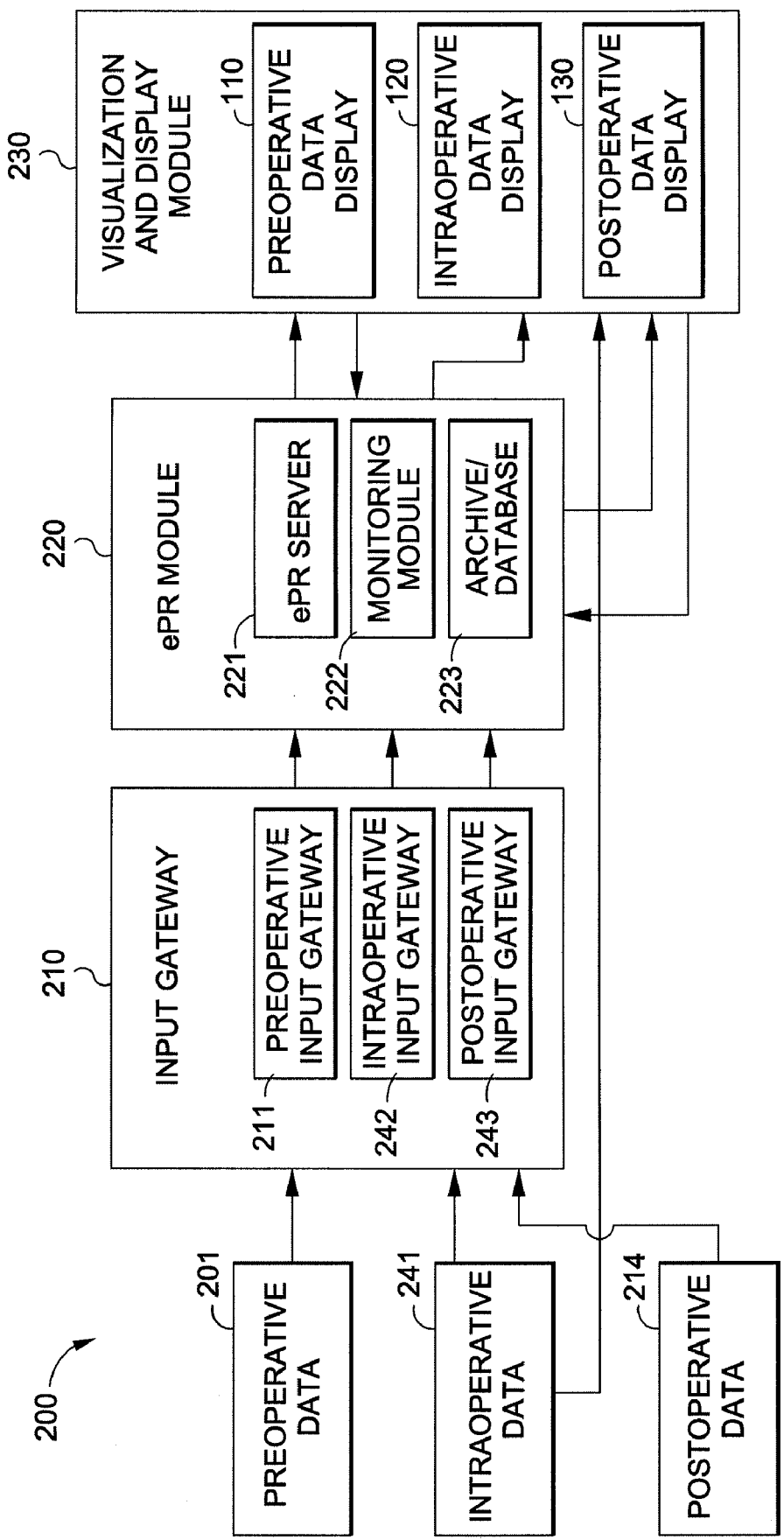
FIG. 2 illustrates a data workflow of the surgical data monitoring and display system according to one embodiment of the invention.

According to one implementation of fault tolerance for the surgical data monitoring and display system illustrated in FIG. 2, a signal from an input device is sent substantially simultaneously to three similar universal interface units associated with preoperative data 201, intraoperative data 241, and postoperative data 244, regardless of whether the signal is itself preoperative data 201, intraoperative data 241, or postoperative data 244. The signal may be sent automatically or manually. If the appropriate interface unit receives and verifies the receipt of the signal, the identical signal in other two interface units can be discarded. If, however, that interface unit does not receive and/or verify receipt of the proper signal, that unit will automatically request the signal from one of the other two interface units. The appropriate interface unit may then transmit the signal to the fault-tolerant input gateway 210, and from there, the signal may be transmitted by the fault-tolerant ePR module 220. In certain embodiments, the probability of success that at least one of the three interface units will receive the signal is 99.999%. Once the signal leaves an interface unit and is received by the fault-tolerant input gateway 210, the responsibility of the interface unit is completed. A similar method may be used if the input signal is an image or another form of data.

According to one implementation of fault tolerance for the surgical data monitoring and display system illustrated in FIG. 2, there are three identical ePR modules 220. One of the three ePR modules 220 serves as the primary ePR module 220 and the other two ePR modules 220 (not illustrated) serve as backups. Each ePR module 220 has three identical ePR servers 321, monitoring modules 322, and archive/databases 323. A signal from an input gateway 211, 242, or 243 is automatically sent to all three ePR modules 220 simultaneously. The signal may then be placed in an ePR procedure queue and archived properly. A failure in any component in the primary ePR module will automatically cause the signal to be sent to the second ePR module, and if that has failed, then the signal is sent to the third ePR module. The visualization and display module 230 is configured to request data from the ePR module 220 for any of the preoperative data display 110, intraoperative data display 120, and postoperative data display 130. The probability of success of the ePR module, with three identical modules, to receive and to transmit proper requested data to the visualization and display module 230 is 99.999%.

The software of the visualization and display module 230 is likewise configured for fault tolerance. For hardware fault tolerance, the preoperative data display 110 and intraoperative data display 120 are backed up by a passive third monitor.

The visualization and display module 230 comprises a preoperative data display 110 for preoperative data, an intraoperative data display 120 for intraoperative data, and a postoperative data display 130. The postoperative data display 130 is used for the display of postoperative documentation of the patient by interactively extracting or otherwise using data from the ePR module 220. In certain embodiments, the postoperative authoring and display module 130 advantageously uses data mining methods for developing metadata usable for knowledge discovery, and to create teaching files for educational purposes.

In certain embodiments, input gateway 210 includes software configured in accordance with the DICOM standard for use with off-the-shelf computers. In certain embodiments, the software is configured to collect data from acquisition interfaces, such as through the development of a DICOM listener/receiver, a non-DICOM data receiver, and a buffer queue for staging data for transmission and/or conversion. In certain embodiments, the software is configured to conduct DICOM conversion by determining which data arriving in the buffer queue will be converted to DICOM, and advantageously use an automatic DICOM data conversion module to convert the data, wherein the automatic DICOM data conversion module uses a rules-based algorithm developed for automatic data conversion. Input gateway 210 further includes a DICOM-send module configured to send data to ePR module 220 in DICOM format, and a non-DICOM-send module configured to send non-DICOM data to ePR module 220 as necessary. Input gateway 210 also includes a DICOM and a non-DICOM verification procedure to verify that data has been conformed to DICOM standards and, in certain embodiments, stored within ePR module 220. Input gateway 210 also includes software configured to confirm that data from acquisition interfaces (e.g., preoperative data 201, intraoperative data 241, and postoperative data 244) are successfully received and stored.

Input gateway 210 yet further includes addendum data integration software that is configured to integrate data with existing study data in ePR module 220. The addendum data integration software is configured to query/retrieve data from ePR module 220 to determine or locate a related study, update ePR module 220 with addendum data, and send to and store the addendum data with the original study in ePR module 220.

As illustrated, ePR module 220 includes an ePR server 221, monitoring module 222, and archive/database 223. These components can be either software or hardware. In certain embodiments, preoperative data 201 is retrieved before surgery and processed by the preoperative input gateway 211 and stored in ePR module 220. In certain embodiments, intraoperative data 241 (e.g., data from the surgery) is retrieved by intraoperative input gateway 242 and stored in ePR module 220 for later use. Sampled intraoperative waveform data can be archived in the archive/database 223 of ePR module 220. In certain embodiments, data stored in the ePR module 220 complies with the DICOM standard.

In certain embodiments, development of the archive/database 223 includes three steps: (1) archive/database 223 schema design, (2) analysis, at a high-level, of the archive/database 223 schema, and (3) validation of the archive/database 223. The archive/database 223 schema design for preoperative data, intraoperative data, and postoperative data includes determining and/or developing any necessary or key data fields related to preoperative data, intraoperative data, and postoperative data and developing data object relationships within the database schema.

The archive/database 223 schema design for preoperative data, intraoperative data, and postoperative data also includes designing a framework utilizing current DICOM standards and Integrating the Healthcare Enterprise (IHE) workflow profiles, and obtaining off-the-shelf database software that supports the ePR archive database 223 based on performance, flexibility, and modularity. The archive/database 223 schema design further includes development of classes and class structure for database tables based on clinical workflow and DICOM standard and IHE workflow profile, designing tools and method(s) to extract input data, including DICOM header information, from image data, and designing tools and method(s) to query data fields based on surgical clinical workflow. The archive/database 223 schema design yet further includes designing tools and methods to update data fields based on clinical workflow, and designing tools and methods to retrieve data for requesting client.

Figure 3A:
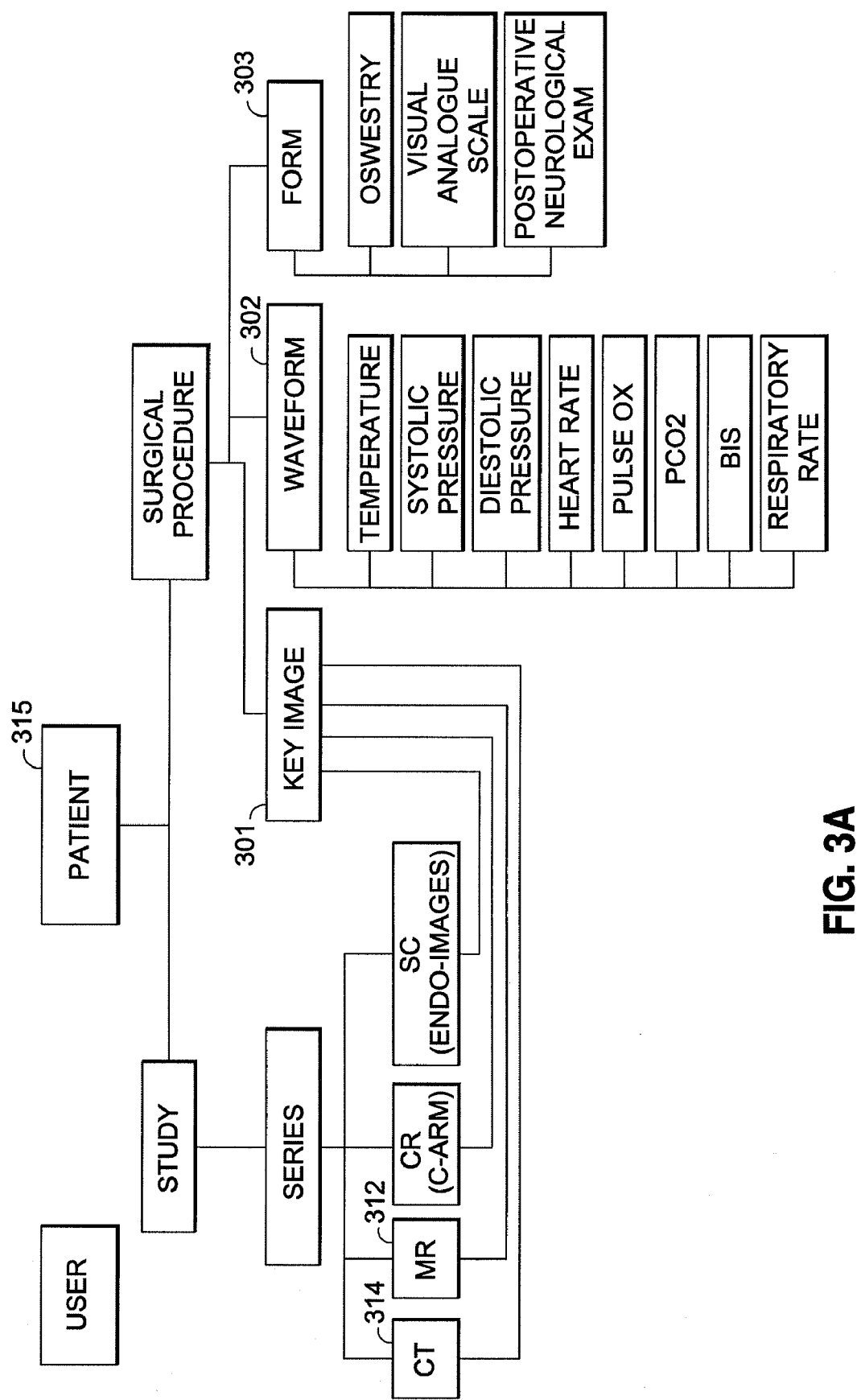
FIG. 3A illustrates a high-level database schema of an electronic patient record (ePR) module according to one embodiment of the invention.
Figure 3B:
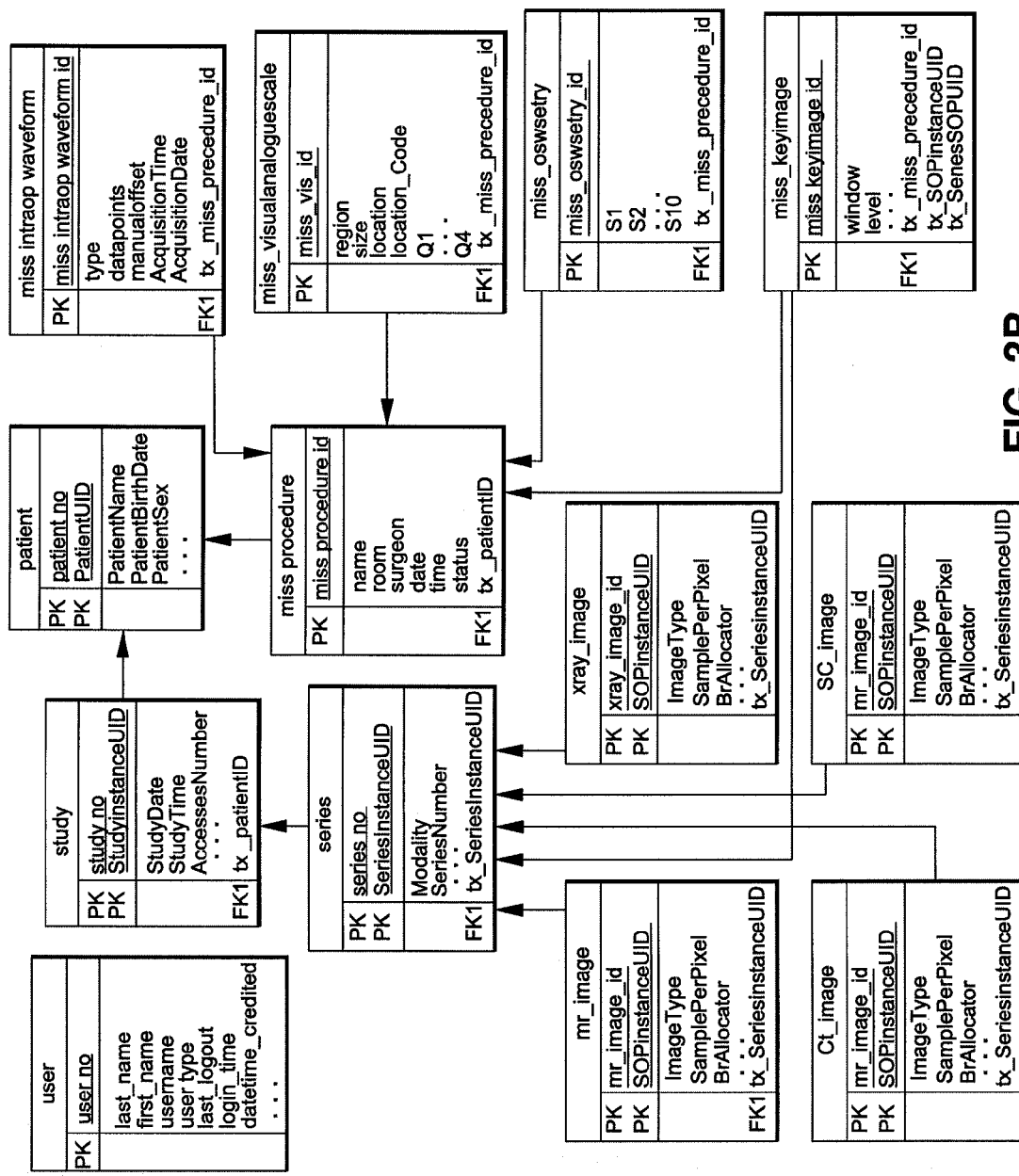
FIG. 3B illustrates a low-level database schema of the ePR module of FIG. 3A according to one embodiment of the invention.
Figure 3C:
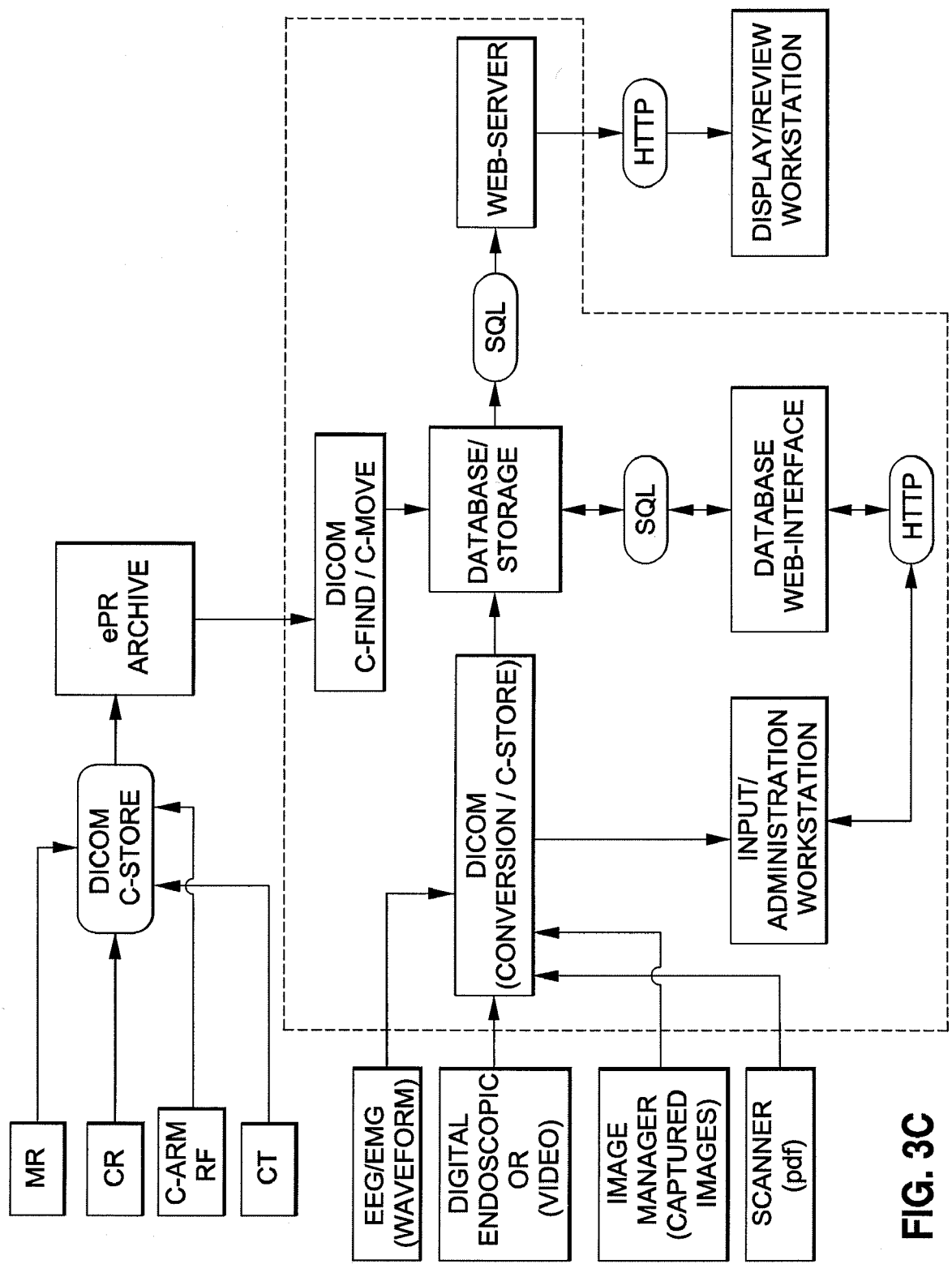
FIG. 3C illustrates a data workflow of the surgical data monitoring and display system according to one embodiment of the invention.

The second step in the development of the archive/database 223 is analysis of the high-level database schema of the ePR module, the low level database schema based on DICOM standard data model, and the preoperative, intraoperative, and postoperative dataflow model, as illustrated in FIGS. 3A-3D. FIG. 3A illustrates a high-level database schema of an ePR module 220 according to one embodiment of the invention. Key images 301 are selected by a surgeon and saved during the preoperative and intraoperative surgical procedure. Intraoperative waveform signals 302 are sampled and archived. Preoperative and postoperative forms 303 are sampled and archived. FIG. 3B illustrates a low-level database schema of the ePR module of FIG. 3A according to one embodiment of the invention. FIG. 3C illustrates a data workflow of the surgical data monitoring and display system according to one embodiment of the invention.

Figure 3D:
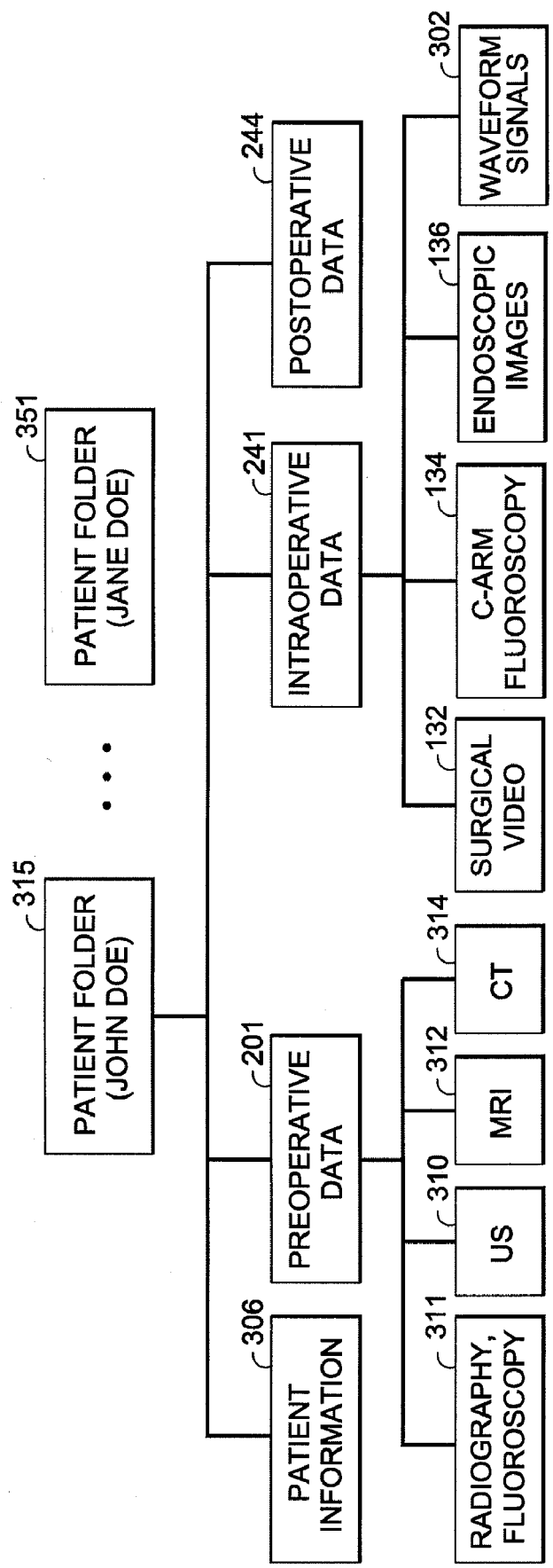
FIG. 3D illustrates another database schema of the ePR module of FIG. 3A according to one embodiment of the invention.

FIG. 3D illustrates a data model of the surgical data monitoring and display system according to one embodiment of the invention. In certain embodiments, the data model is based on the DICOM standard. The data model categorizes and processes patient information 306, preoperative data 201, intraoperative data 241, and postoperative data 244 using a multimedia data model. In the embodiment illustrated, information is organized according to the patient with whom it is associated. Information for patient John Doe 315 is illustrated, although information may be stored for any number of patients 351.

The information associated with John Doe 301 includes patient information 306, preoperative data 201, intraoperative data 241, and postoperative data 244. In certain embodiments, the preoperative data 201 includes patient information 306. In addition to the types of information described above, preoperative data can also include information concerning other patients and/or teaching cases, procedures, surgical protocol, or instruction manuals, and image information. The image information can include data such as images from radiography 311, including myelograms, fluoroscopy, MRI 312, X-ray tomograms, computed tomography (CT) 314, and/or ultrasound (US) 310. In addition to the types of information described above, in the embodiment illustrated intraoperative data 241 includes information from surgical video 132, C-ARM fluoroscopy 134, endoscopic images 136, and waveform signals 302, such as from EEG 138, EMG 140, EKG 141, and patient biometric identification 135.

In certain embodiments, the ePR data model comprises methods to advantageously arrange and process patient information, preoperative data, intraoperative data, and postoperative data for seamless retrieval and display of the retrieved data on the preoperative data display 110, intraoperative data display 120, and postoperative data display 130, as well as other workstations in the surgical data monitoring and display system 100. In certain embodiments, special methods are used to categorize and process preoperative data 201 like US data 310, radiography, fluoroscopy 311, CT 314, and MRI 312 and their three dimensional rendering, such as for surgical planning. In certain embodiments, special methods are used to categorize and process intraoperative data 241 including surgical video 132, C-arm fluoroscopy 134, endoscopic images 136, and waveform signals 302. In certain embodiments, special methods are used to categorize and process postoperative data 244 for patient documentation and training materials.

Returning to FIG. 2A, the third step in the development of the archive/database 223, validation of the archive/database 223, involves three steps. The first sub-step is to use sample preoperative data, intraoperative data, and postoperative data from the preoperative input gateway 211, intraoperative input gateway 242, and postoperative input gateway 243 to test the database design, conversion tools, extraction methods, and receiver modules, and validate the extraction and insertion of data into data tables and data field populations. The second sub-step is to refine the archive/database 223 and the database schema based on evaluation of the prior results. The final substep is to test retrieval methods for requesting information from clients, such as a hospital, and to validate data retrieval results from ePR server 221 to confirm the operation integrity of the ePR system.

In certain embodiments, postoperative input gateway 243 is configured to transmit relevant postoperative data to ePR module 220 as well as incorporate preoperative data 201 and intraoperative data 241. Postoperative input gateway 243 is also configured to conform postoperative data to selected image and data standards in accordance with data that has previously been processed in the preoperative input gateway 211 and intraoperative input gateway 242. Postoperative input gateway 243 is further configured to organize preoperative data 201, intraoperative data 241, and postoperative data 244 of the same patient in the archive/database 223.

As discussed above, the ePR server 221, monitoring module 222, and archive/database 223 components of the ePR module 220 can select information received from the input gateway 210 to display using the visualization and display module 230. In certain embodiments, any interface or device having the capability to conduct the functions of the fault-tolerant ePR module 220 can be used.

In certain embodiments, each of the ePR module 220, input gateway 210, and visualization and display module 230, as well the components that comprise them, can be networked or otherwise connected according to any method known in the art. For example, each may be a node on a network connected using a wired connection or a wireless connection. In certain embodiments, any of the nodes may be available remotely using an Internet connection. In certain embodiments, any or all of the nodes may be locally available.

Figure 4A:
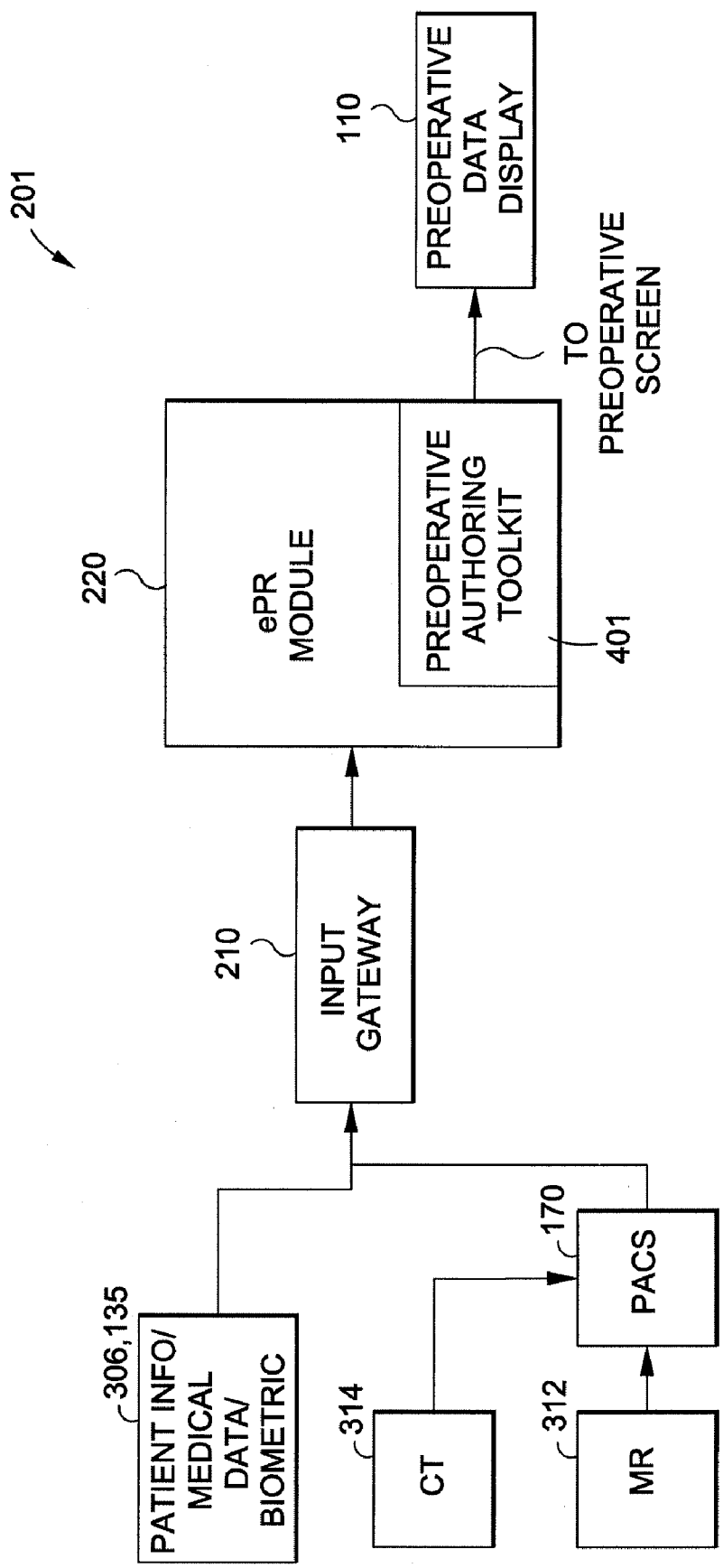
FIG. 4A illustrates a preoperative workflow according to one embodiment of the invention.

FIG. 4A illustrates a preoperative workflow according to one embodiment of the invention. Input gateway 210 receives patient information 306 and biometric information 135 directly, but receives CT and MR data through PACS server 170. Input gateway 210 is configured to transmit this information to ePR module 220, which advantageously features an authoring toolkit 401 with which to evaluate, plan, and approve authored preoperative data that may be displayed on preoperative data display 110.

Figure 4B:
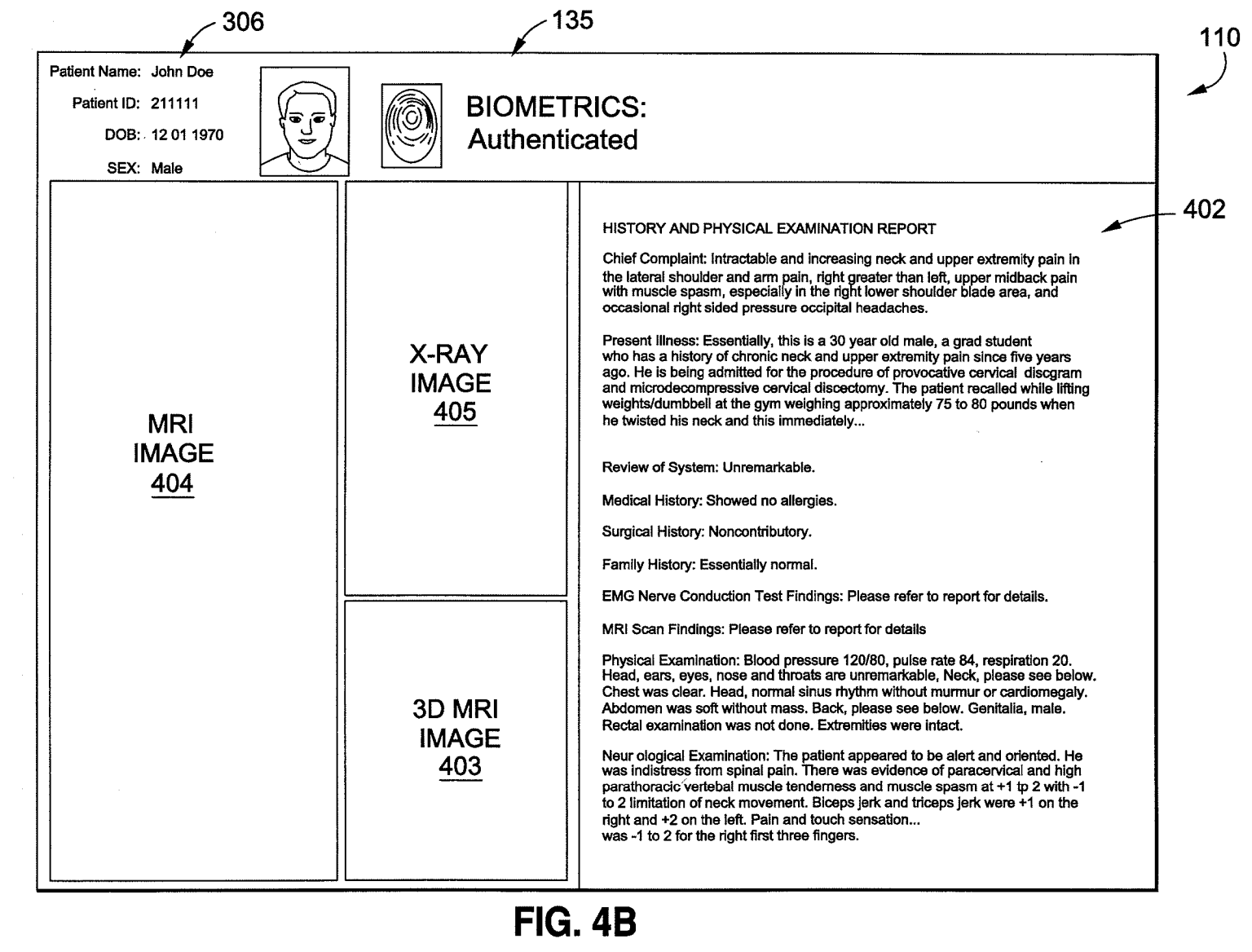

FIG. 4B illustrates a sample screenshot from a preoperative data display 110 according to one embodiment of the invention. The preoperative data display 110 includes patient information 306, such as the patient's name, identification number, date of birth, and sex, as well as the patient's biometric information 135, such as a photograph of the patient and the patient's fingerprint. The preoperative data display 110 also includes the patient's history and diagnoses 402, as well as the patient's consultation sagittal and transversal MRI 404. The preoperative data display 110 further includes an anteroposterior (AP) X-ray image 405, and the patient's reconstructed 3-D MRI image 403. The data displayed on the preoperative data display 110 can be organized according to user preference. The surgical data monitoring and display system is further configured to store the user preference for later use.

Figure 5A:
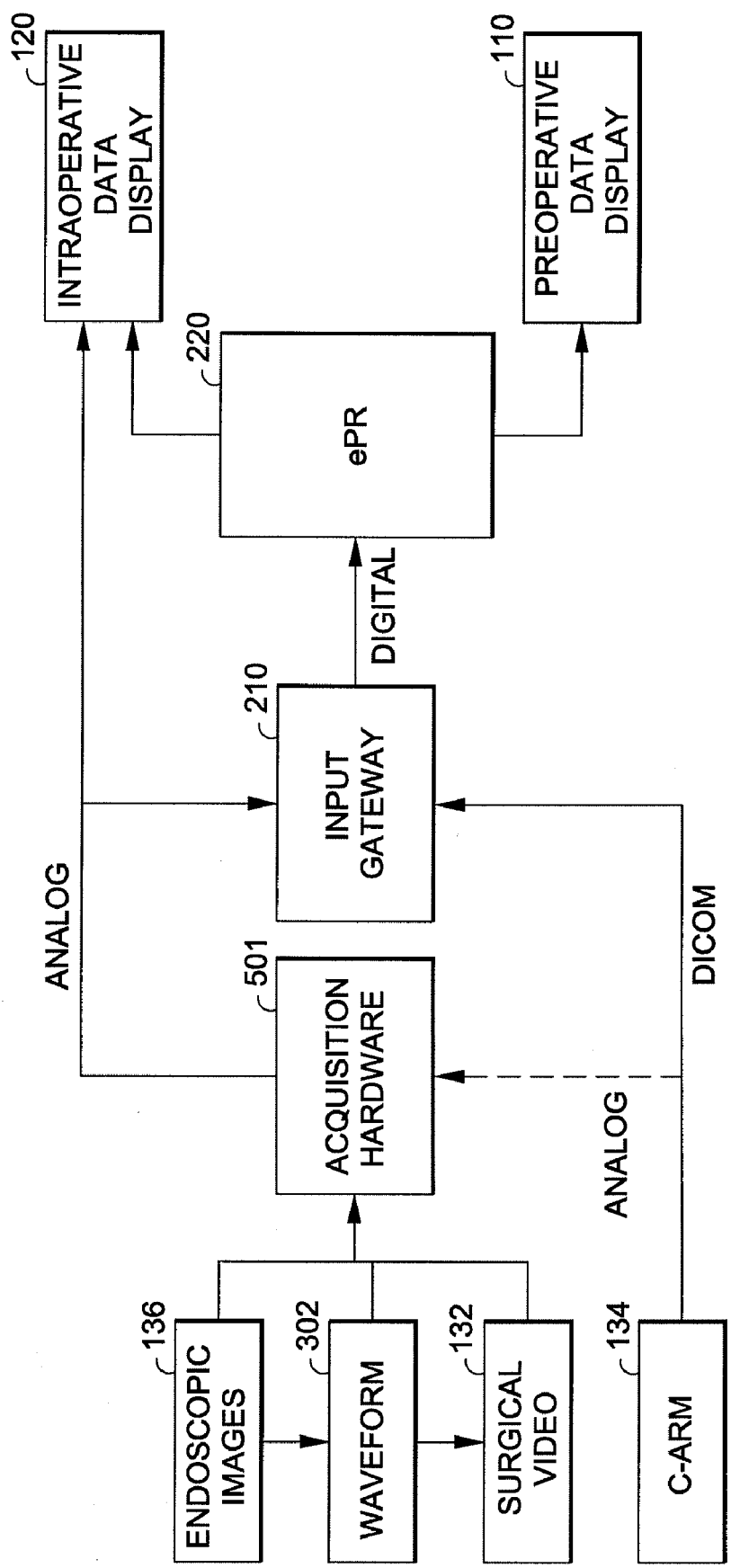
FIG. 5A illustrates an intraoperative workflow featuring intraoperative data acquisition hardware according to one embodiment of the invention.

FIG. 5A illustrates a intraoperative workflow featuring intraoperative data acquisition hardware 501 according to one embodiment of the invention. Acquisition hardware 501 receives endoscopic images 136, waveform data 302, and surgical video 132 directly, and also receives C-arm data in analog format. Acquisition hardware 501 will be discussed in further detail below with reference to FIGS. 5C-5F. Input gateway 210 receives C-arm data in DICOM format and information from acquisition hardware in analog format. Input gateway 210 converts the analog information into digital format, and transmits the information in digital format to ePR module 220. Preoperative data display 110 displays information from ePR module 220, and intraoperative data display 120 displays information from ePR module 220 and acquisition hardware 501. In certain embodiments, intraoperative data display can advantageously feature interactive probe positioning, such as by using simultaneous freeze frame and live video display, as discussed in further detail with reference to FIG. 5G.

Figure 5B:
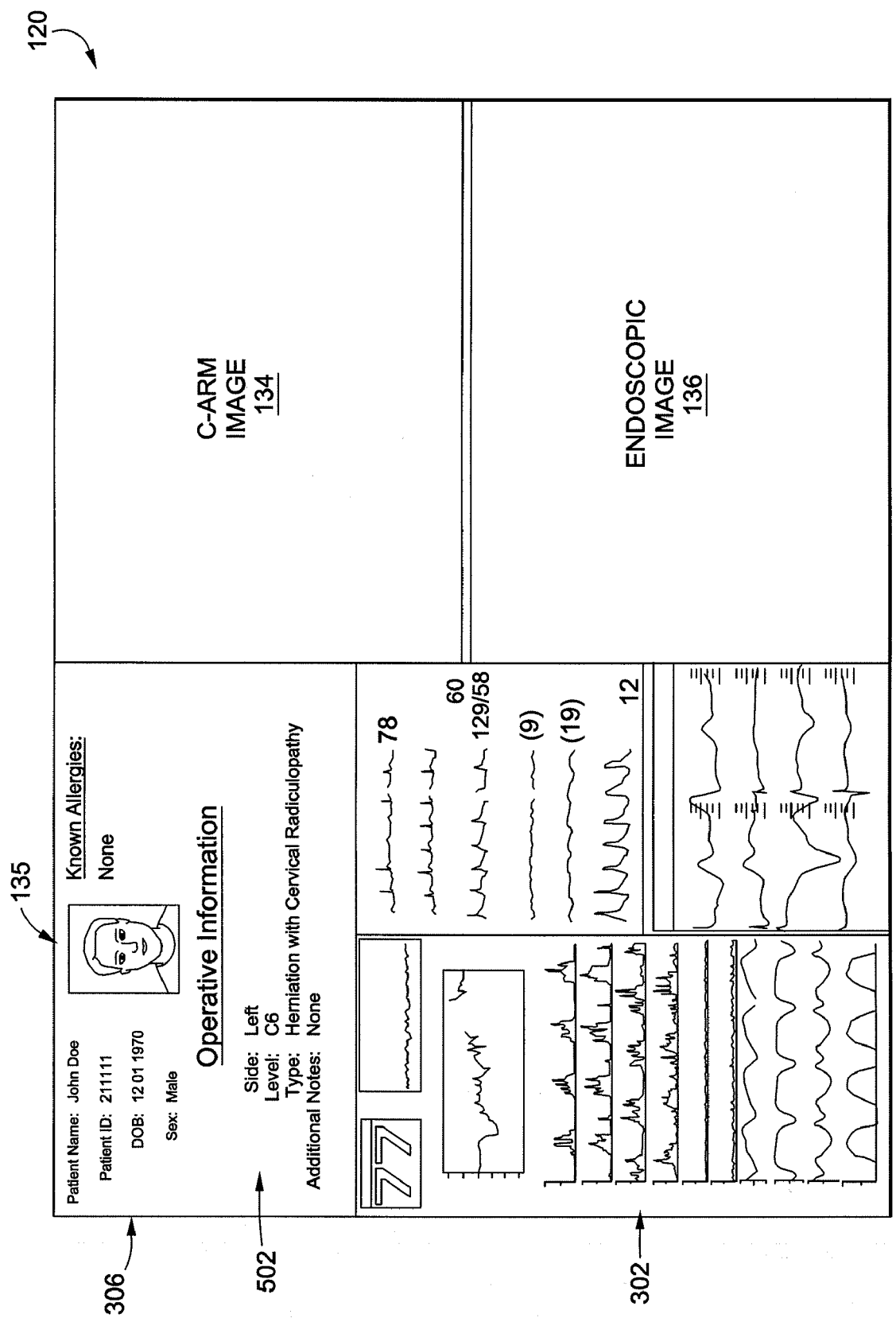
FIG. 5B illustrates a sample screenshot from an intraoperative data display according to one embodiment of the invention.

FIG. 5B illustrates a sample screenshot from an intraoperative data display 120 according to one embodiment of the invention. The intraoperative data display 120 includes patient information 306 and biometric information 135, as discussed above with reference to FIG. 4B. The intraoperative data display 120 also includes information on the surgical procedure to be performed 502, including, for example, fields for side, level, type, and additional notes. The intraoperative data display 120 further includes intraoperative (e.g., real-time) waveform data 302, C-arm fluorographic images 134, and endoscopic images 136. They are organized by a surgeon's preference. The data displayed on the intraoperative data display 120 can be organized according to user preference. The surgical data monitoring and display system is further configured to store the user preference for later use.

In certain embodiments, in order to display a plurality of waveforms 302 on the intraoperative data display 120, the individual waveforms 302, each having its own independent clock, need to be synchronized against the master clock, as discussed above. Additionally, a clinically acceptable display time until should be selected to display all of the waveforms 302 and/or images 134 and 136. A user can also select locations to display the waveforms 302 on the intraoperative data display 120.

In certain embodiments, various techniques and methods are used to systematically organize and display data on the intraoperative data display 120. These techniques and methods may also be applied to the preoperative data display 110 and postoperative data display 130. For example, in certain embodiments, the intraoperative data display may be placed toward the left-hand side of the surgeon, as illustrated in FIG. 1, at a height above surgical equipment and in a position convenient to the surgeon's vision, thereby reducing the time and eye motion required for a surgeon to look up from a surgical procedure to view data that is continuously updated. Likewise, the preoperative data display 110 may be placed toward the right-hand side of the surgeon, also as illustrated in FIG. 1, at a height above surgical equipment and in a position convenient to the surgeon's vision. In other embodiments, the locations of the intraoperative data display 120 and preoperative data display 110 may be interchanged.

In certain embodiments, a large display may be used for any of the preoperative data display 110, intraoperative data display 120, and postoperative data display 130. In certain embodiments, a small display may be used. In situations where a small display is used and/or where all data sources are not displayed on a display, a subset of the available data sources (e.g., preoperative data 201, intraoperative data 231, and postoperative data 244) may be selectively displayed. For example, if there are twenty available data sources that may be displayed on a display screen, and there is only available space for ten data sources to be displayed, then the system may selectively choose, by a pre-programmed system default, which ten sources may be displayed. Data sources may be selected, changed, enlarged, moved, or otherwise affected by, for example, a control (e.g., a button panel) within reach of the surgical table. In certain embodiments, data may be selected for display using a remote control device, such as a wireless, handheld control panel. For example, a button panel may be used to switch from a single static image to a multiple image panel, or to use zoom and scroll features.

In certain embodiments, waveform data are not displayed continuously, but instead are displayed digitally at a give interval determined by a surgical procedure, built-in algorithm, and/or a given patient condition. In certain embodiments, intraoperative data is configured and/or processed to be displayed at an appropriate or predetermined times on the intraoperative data display 120. For example, blood pressure may be displayed for an interval of ten seconds followed by the display of the patient's heart rate for an interval of ten seconds. As another example, data sources which constantly change (e.g., heart monitoring data) may be displayed more often and for longer period than data that changes less often (e.g., blood pressure). In certain embodiments, images are displayed in their original image quality, while in other embodiments, they may be displayed using a different quality. In certain embodiments, intraoperative data can be sent directly to and displayed on the intraoperative data display 120 without any delay, while in certain embodiments, intraoperative data may be delayed before being displayed on the intraoperative data display 120.

In certain embodiments, the surgical data monitoring and display system includes an alert system configured to call attention to data, such as for use with intraoperative data 241 and preoperative data 201. The alert system may be software configured in the input gateway 210. The alert system may provide an audible or visible alert, such as, for example, providing an audible alarm when an input signal is outside a preset threshold value for patient protection. This is especially advantageous for intraoperative data, which may undergo a significant change in state during the performance of a medical procedure thereby needing the attention of the physician. For example, a patient's blood pressure may incur a significant drop during surgery, and this intraoperative data would be brought to the attention of the surgeon by the alert system. Visible alerts can include automatically moving the selected intraoperative data on the intraoperative data display 120 to a more prominent location, enlarging the selected intraoperative data, changing the color of the selected intraoperative data, and flashes of light, and audible alerts can include any various type of sound.

Figure 5C:
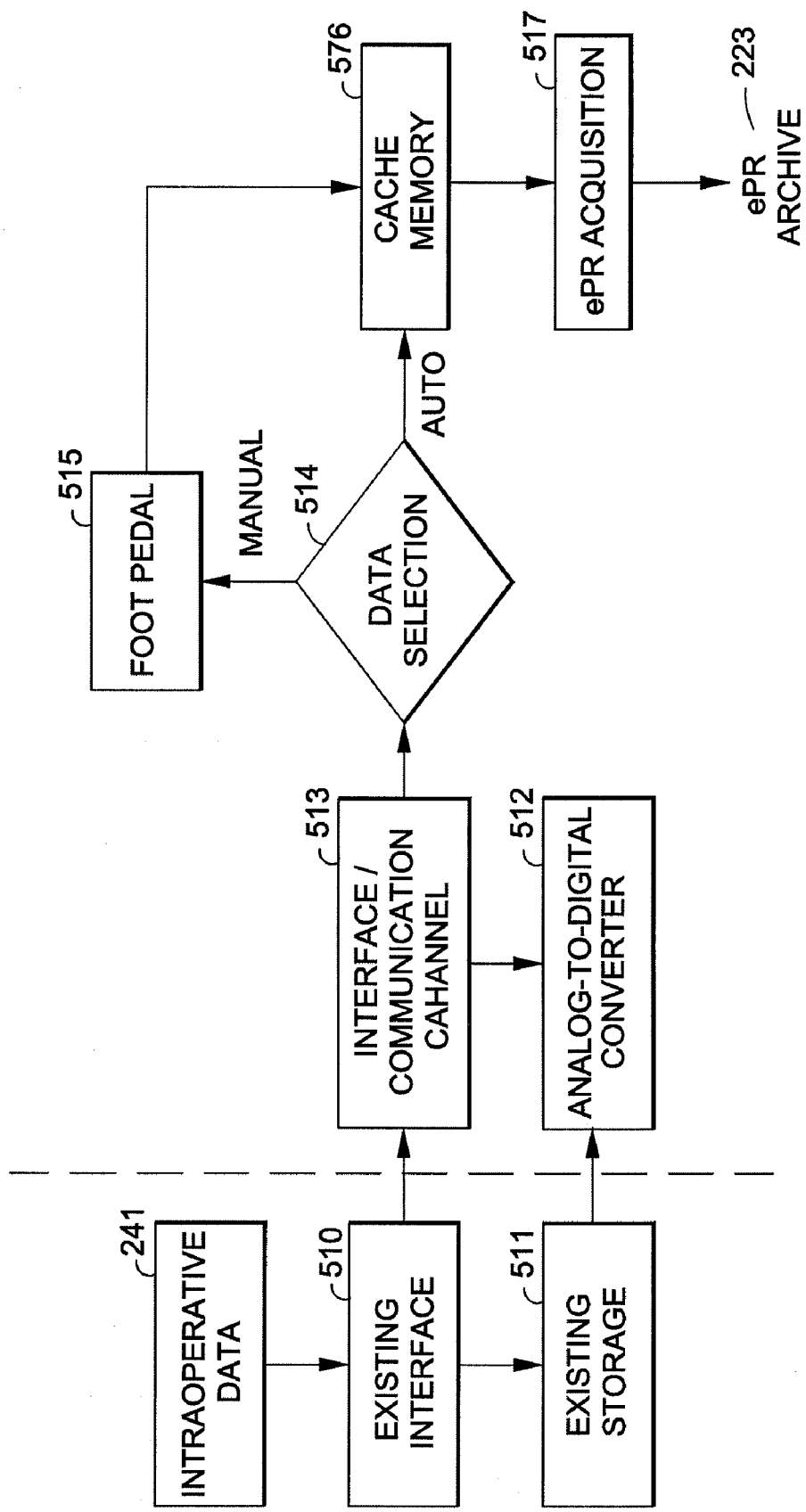
FIG. 5C illustrates a data workflow for acquiring and storing intraoperative data using the intraoperative data acquisition hardware of FIG. 5A according to one embodiment of the invention.

FIG. 5C illustrates a data workflow for acquiring and storing intraoperative data using the intraoperative data acquisition hardware of FIG. 5A according to one embodiment of the invention. The surgical data monitoring and display system acquires intraoperative data 241 during surgery. For example, intraoperative waveform data such as vital signs are collected continuously and sampled at a predetermined interval depending on the type of waveform, surgical procedure and the patient condition. Once an interval value is determined for each waveform, the interval value is preset as the default for that waveform. In certain embodiments, these values are then archived in real-time. For example, sequential intraoperative fluorographic images can be taken when a surgeon needs to review and confirm a surgical site by a radiological technologist near the surgical table. Several of the intraoperative fluorographic images may then be selected to determine the proper surgical site, and then archived. Endoscopic images can likewise be taken continuously during the surgical procedure. A surgeon can select to archive in existing storage 511 a sequence of images periodically. Thus, intraoperative data 241 may be sent through a preexisting interface and stored in existing storage.

In certain embodiments, intraoperative data 241 can be retrieved from storage 511 and converted from analog to digital format 512, if necessary, and sent to an interface/communication channel 513. The interface/communication channel can then send the data for manual selection 514 by the physician, such as by using a foot pedal 515, or automatically for acquisition 517 and storage in ePR archive 223, such as by using a large cache memory 516 as an intermediary. The foot pedal 515 can be used when a surgeon decides to keep a certain fluorographic image, or a sequence of endoscopic images during the surgery. The foot pedal may feature several selection-button groups. One group of buttons can allow images to be archived, and another group of buttons can control the currently displayed single camera endoscopic video with split screen for adjusting the probe location, as described in further detail with reference to FIG. 5G. Another group of buttons can be used for display functions, such as zooming, scroll, changing between a static mode and dynamic mode. In certain embodiments, a hand panel may be used instead of a foot pedal. In certain other embodiments, other input devices may be used.

Figure 5D:
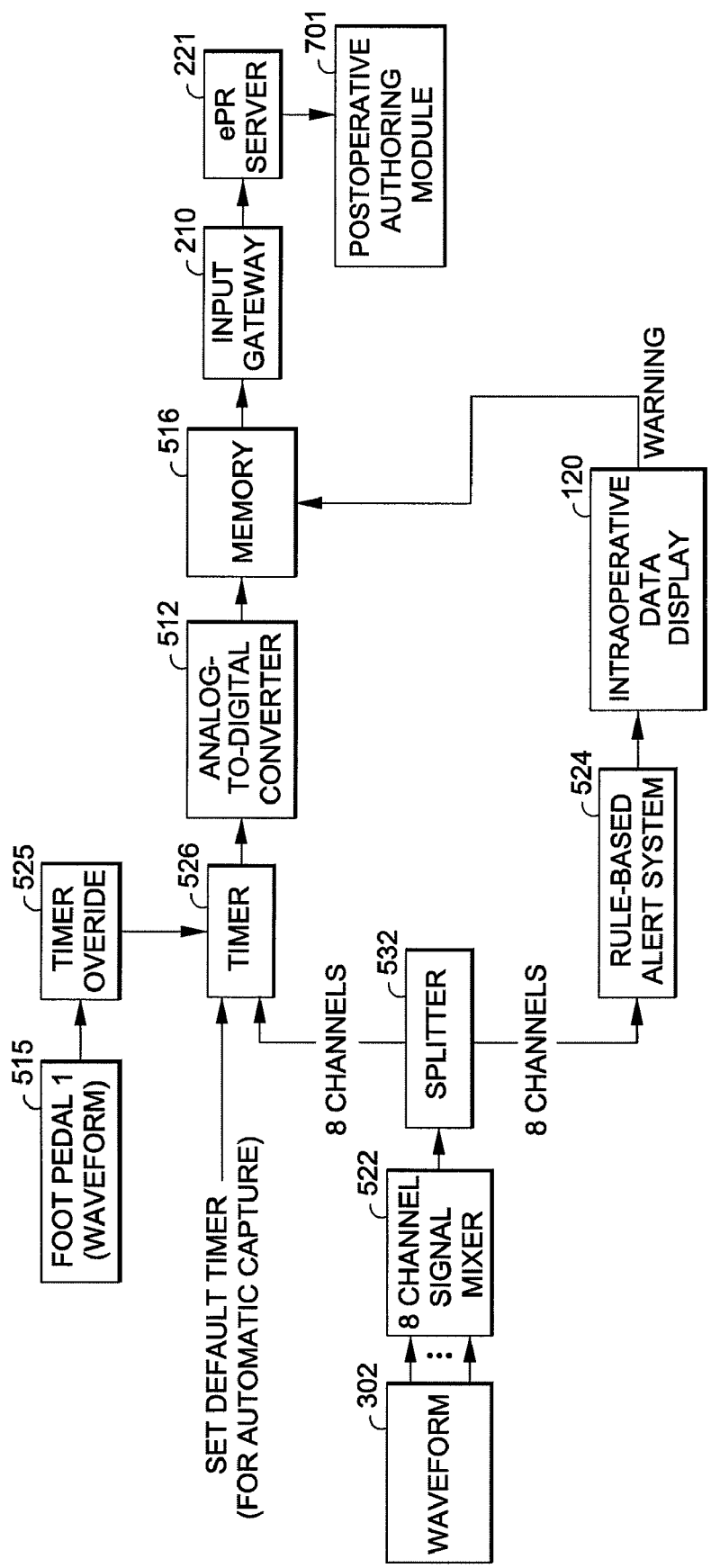
FIG. 5D illustrates a data workflow for acquiring and storing intraoperative waveform data using the intraoperative data acquisition hardware of FIG. 5A according to one embodiment of the invention.

FIG. 5D illustrates a data workflow for acquiring and storing intraoperative waveform data using the intraoperative data acquisition hardware 501 of FIG. 5A according to one embodiment of the invention. Intraoperative waveform data 302, which are substantially continuously displayed on intraoperative data display 120, are automatically captured at predefined intervals set by a default timer 526. Additional sets of waveforms can be captured using a foot pedal 515 or other input device, which is configured using timer override 525 to override the default time interval mechanism. The system also features a rule-based alert system 504 to provide alerts if the acquired waveforms 302 fall within the bounds set by the rule-based alert system 504. For example, if a heart rate waveform exceeds a certain threshold predefined by the rule-based alert system 524, an alert is issued, as discussed above. The alert functionality is provided by splitting 523 the acquired waveform into separate signals. Although the waveforms are illustrated as being received using an eight channel mixer 522 and then split 523 into separate eight channel signals, other numbers of channels and types of signals, signal mixers, and splitters can be used. The output intraoperative waveform data from the timer then passes to audio-to-digital converter 512, if necessary, and then goes through memory 516 and through to the input gateway 210. The intraoperative waveform data is then sent from the input gateway 210 to ePR server 221, and then sent to postoperative authoring module 701, discussed in further detail below with reference to FIG. 7A.

Figure 5E:
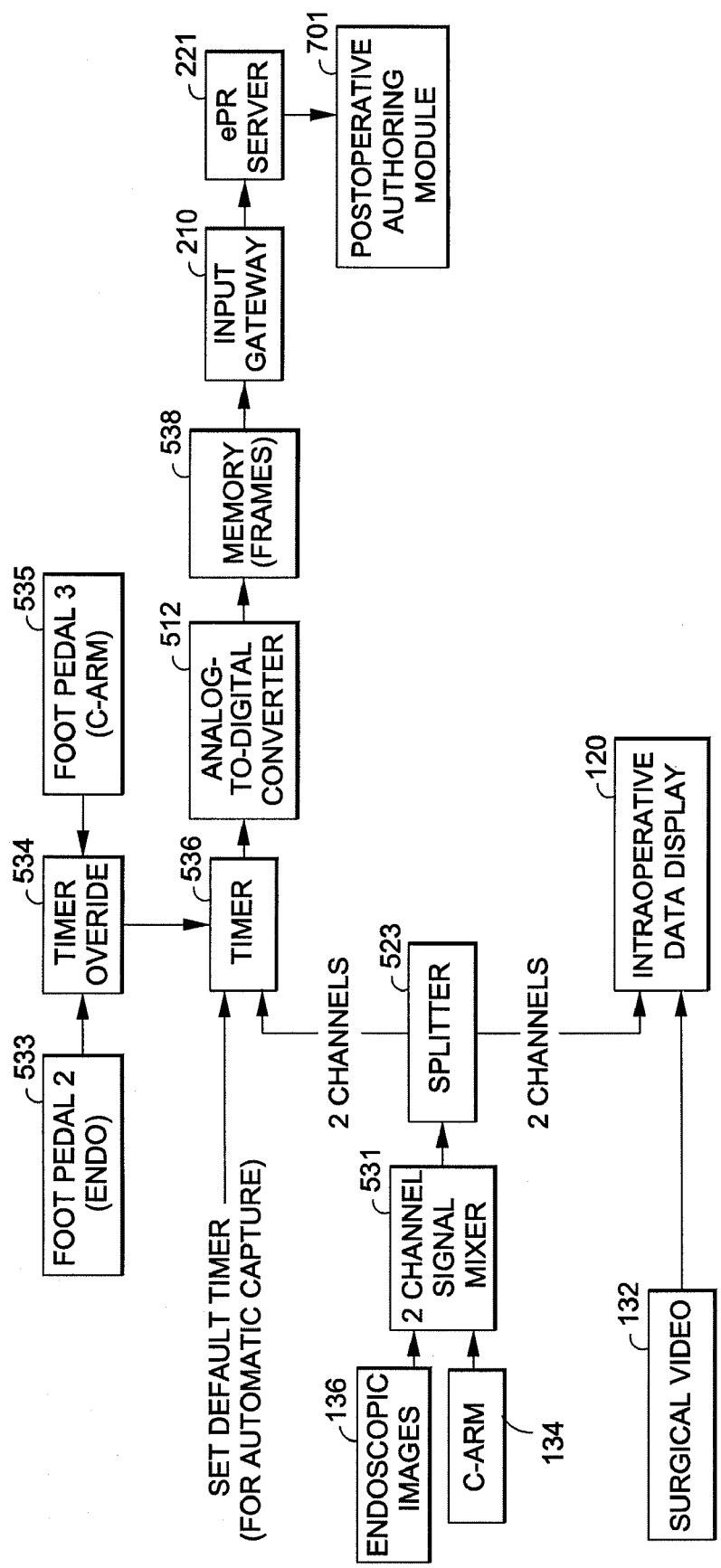
FIG. 5E illustrates a data workflow for acquiring and storing intraoperative videos and images using the intraoperative data acquisition hardware of FIG. 5A according to one embodiment of the invention.

FIG. 5E illustrates a data workflow for acquiring and storing intraoperative videos and images using the intraoperative data acquisition hardware 501 of FIG. 5A according to one embodiment of the invention. In the illustrated configuration, a first video feed including endoscopic images 136 and C-arm video 134 are mixed in a two channel signal mixer 531 and then split in a splitter 532, such that the first of the two split video feeds can be displayed on a intraoperative data display 120 along with surgical video 132. The second, remaining video feed from the splitter 532 is then automatically captured on predefined intervals set by a default timer 536. Additional sets of images from the video feed can be captured using foot pedals 533 and 535 or other input devices configured using timer override 534 to override the default time interval mechanism 536, such that each input device designated to manually capture an image from a portion of the video feed. Although the waveforms are illustrated as being received using a two channel mixer 531 and then split 532 into separate two channel signals, other numbers of channels and types of signals, signal mixers, and splitters can be used. The output intraoperative video and image data from the timer 536 then passes to audio-to-digital converter 512, if necessary, and then goes through memory 538 and through to the input gateway 210. The intraoperative video and image data is then sent from the input gateway 210 to ePR server 221, and then sent to postoperative authoring module 701.

Figure 5F:
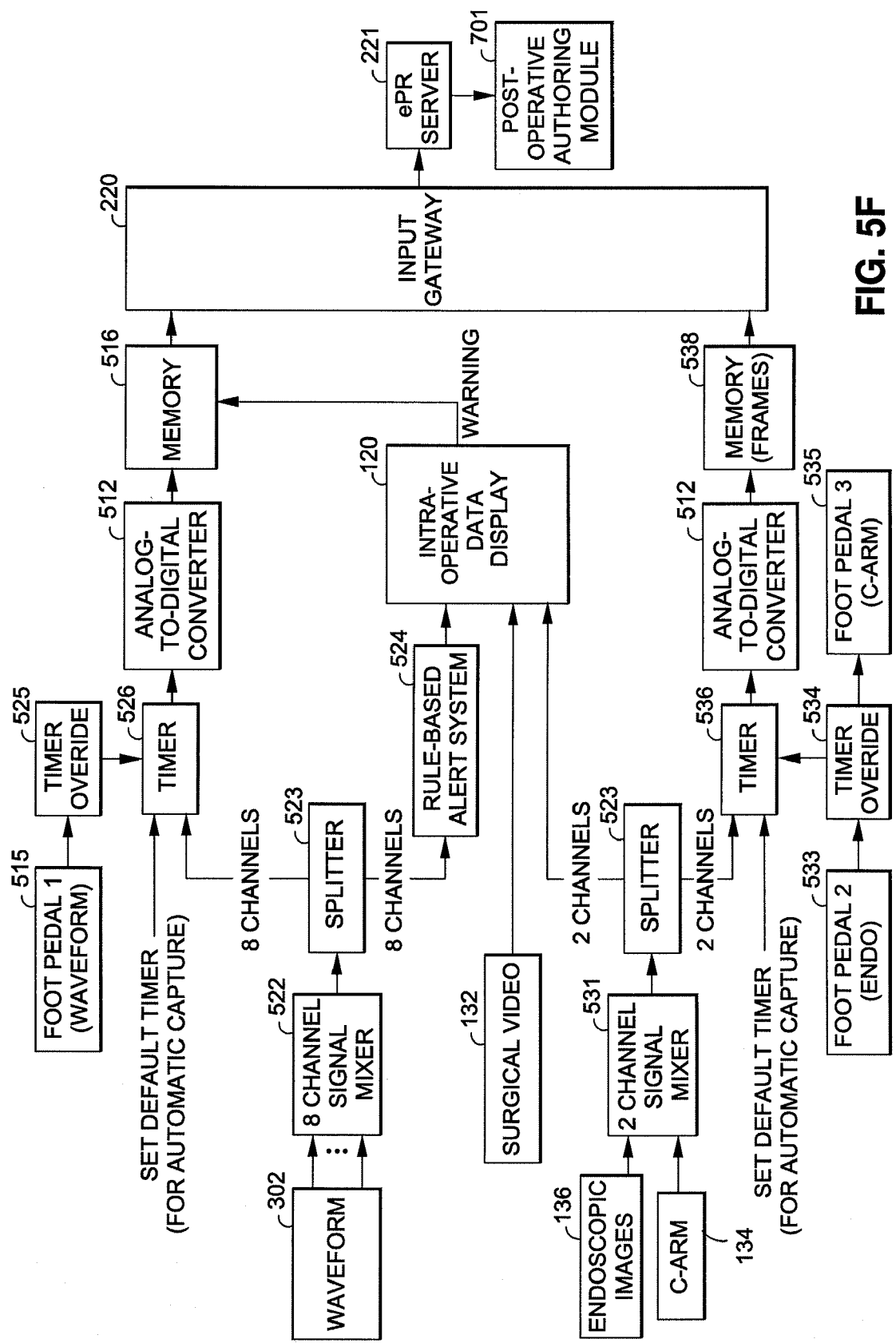
FIG. 5F illustrates a data workflow for integrating the features of FIGS. 5D and 5E according to one embodiment of the invention.

FIG. 5F illustrates a data workflow for integrating the features of FIGS. 5D and 5E according to one embodiment of the invention. FIG. 5F illustrates only one possible integrated configuration of the two system; other integrations of the two systems can also be configured.

Figure 5G:
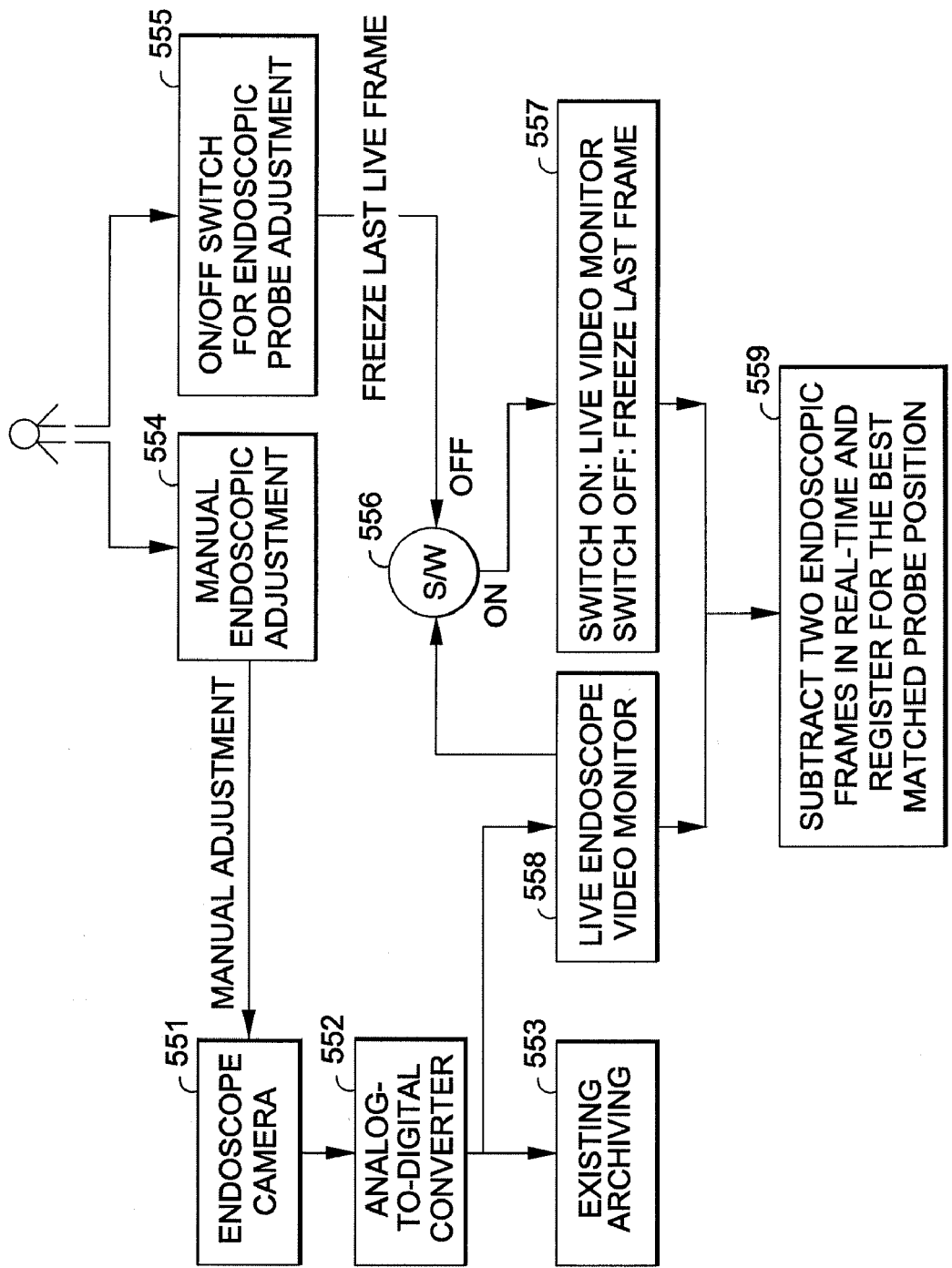
FIG. 5G illustrates a data workflow for using a single camera endoscopic system and/or other acquisition device with a playback mechanism for interactive endoscopic probe position correction during surgery according to one embodiment of the invention.

During an endoscope-assisted surgical procedure, a surgeon may need to change the currently inserted endoscopic probe for a different operation, for example, from a coarse abrasion to a finer abrasion. When the new probe is replacing the existing probe, the surgeon may need to assure the position of the new probe is the same as that of the removed probe. FIG. 5G illustrates the method of using a single camera endoscopic system and/or other acquisition device with a playback mechanism for interactive endoscopic probe position correction during surgery according to one embodiment of the invention. In certain embodiments, endoscopic image data is displayed using two displays, such as two independent monitors or a split screen monitor, while in other embodiments, a single display is used. The endoscopic image provided from the endoscopic probe that was removed is frozen on one side of the screen and the live endoscopic image from the newly inserted probe is displayed on another side of the screen.

The method begins by powering a first endoscope camera 555 and manually positioning the first endoscope camera 554 in a target location. At the target location, the image from the first endoscope camera is frozen 557 using a switch 556. The frozen image remains displayed on the screen. Next, a second endoscope camera is powered on 551 and its data is converted from analog to digital format 552. The digital data is stored in existing archiving 553, and also displayed on screen 558 alongside the frozen image. The digital data from the second endoscope camera is then subtracted from the frozen image 559. In certain embodiments, digital subtraction is used. Digital subtraction between both images is performed in real-time by a customized digital subtraction circuit board chip integrated with the single camera endoscopic video (CCD). In certain embodiments, digital subtraction can be performed at a rate of thirty frames per second. A built-in root-mean-square error (RMS) measurement of the subtracted image chip can compute and displays the RMS number continuously during each subtraction. The smallest RMS error in the sequence is depicted adjacent to the continuous changing sequential numbers on the monitor, and recorded. After a predetermined time, the second probe position with the smallest RMS error is chosen by the surgeon as the position of the second probe. The surgeon can either guide the second probe to the registered position by matching the RMS error manually or the probe can be guided through a six-degree-of-freedom robot arm.

This method has many advantageous features. A surgeon may continue to adjust or otherwise move an endoscopic camera while the image feed from the camera is displayed on the remaining portion of the display, near the captured image of the target location. Should the surgeon desire to move the endoscopic camera back to the target location, the surgeon may compare the live feed on the display screen with the captured image, and determine that when those two images match, the endoscopic camera has returned to the target location. The surgeon may be assisted in his comparison by the use of various image subtraction algorithms that assist in determining a match between the captured image and the image from the live feed, as discussed above.

Figure 6:
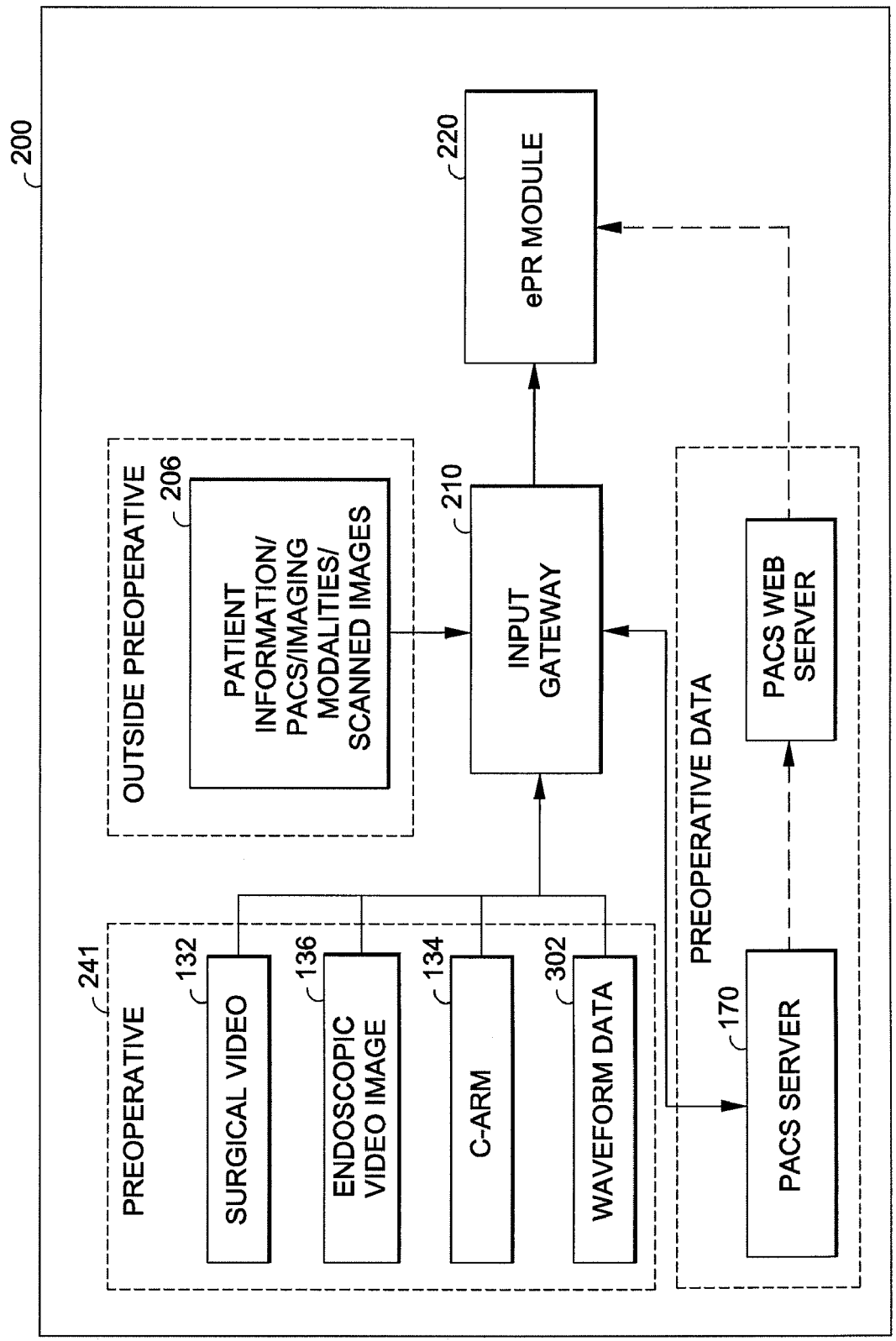
FIG. 6 illustrates a data workflow for preoperative and intraoperative data according to one embodiment of the invention.

FIG. 6 illustrates a data workflow for preoperative and intraoperative data according to one embodiment of the invention. Input gateway 210 can be configured to receive preoperative data from local sources, such as from PACS server 170, as well as remote sources, such as remote imaging modalities 206. The input gateway 210 can be configured to receive intraoperative data such as surgical video 132, endoscopic video images 136, C-arm fluoroscopic images 134, and waveform data (e.g., EEG 138, vital signs 139, EMG 140, EKG 141, and output from a laser generator 142). Input gateway 210 is configured to transmit data to ePR module 220, which can also receive preoperative data directly.

It is important that a surgeon has access to preoperative data, intraoperative data, and postoperative data of the patient after a surgical procedure in order to assess the procedure's outcome. Preoperative, intraoperative, and postoperative data are organized in the ePR module 220, which can be configured for any type of surgical operation using corresponding computer algorithms. For example, a surgeon may summarize and dictate a surgical procedure in detail using preoperative and postoperative patient condition outcomes. A surgeon may also want to evaluate, quantify, and record acute and chronic pain as quantitative parameters in order to measure the success of a surgical procedure. Consequently, a post-processing module is helpful for organizing preoperative, intraoperative, and postoperative data and information into a data and analysis module, such as ePR module 220, accessible to a surgeon and other healthcare practitioner in a patient care area.

In certain embodiments, postoperative processing includes collecting postoperative data 244, postoperative input gateway 243, and postoperative display module 130, which may send or receive information to or from ePR module 220. In certain embodiments, there are three postoperative time phases wherein pertinent data are collected.

A first time phase is immediately after the surgery, or immediate postoperative outcome, such as for example in a recovery room, where clinical information is collected, such as, for example, vital sign information, neurological status, immediate postoperative outcome (e.g. pain response and neurological function, both motor and sensory, questionnaires), and MRI scans. A second time phase is the intermediate postoperative outcome, which is a time period of up to two months after the completion of the surgical procedure. During this second time phrase, information from questionnaires and MRI scans may be collected. The third time phase is the long term patient outcome, which is a time period of up to six months after the completion of the surgical procedure, wherein information from questionnaires and MRI scans may also be collected. Questionnaires may prompt a patient for information related to nursing and patient status forms. In certain embodiments, many types of questionnaires may be used, such as, but not limited to, questionnaires for medical record/history summation, preoperative take home questions (such as a patient diagnosis diagram), history and physical form, pre-anesthesia evaluation form, preoperative assessment/surgical checklist, post-anesthesia nursing record, the Oswestry disability index for back pain, and quadruple visual analogue scale.

Pain is an important parameter in measuring the success of a surgical procedure, and therefore is also an important source of postoperative data. In certain embodiments, two methods of evaluating chronic and acute pain are configured in the postoperative data display 130. A first method is to use MRI information to measure the volume of protrusion of a lesion, which indicates the impingement on a nerve as a means to determine chronic pain arising from a surgical area. Mathematics and computer algorithms using three-dimensional MRI images can also be used to analyze lesions on MRI images. Quantitative comparison between pre-surgical and post-surgical MRI scans is then used as input data to determine a level of pain. In certain embodiment, heart rate variability can also be used to measure a degree of acute pain. Real-time heart rate during preoperative, intraoperative, immediate postoperative, intermediate postoperative, and long-term postoperative periods can be collected and organized in the ePR module 220 to compute differences in heart rate at different times. Variability can be correlated with acute pain of the patient. Algorithms for measuring the variability are configured in the surgical data monitoring and display system.

Figure 7A:
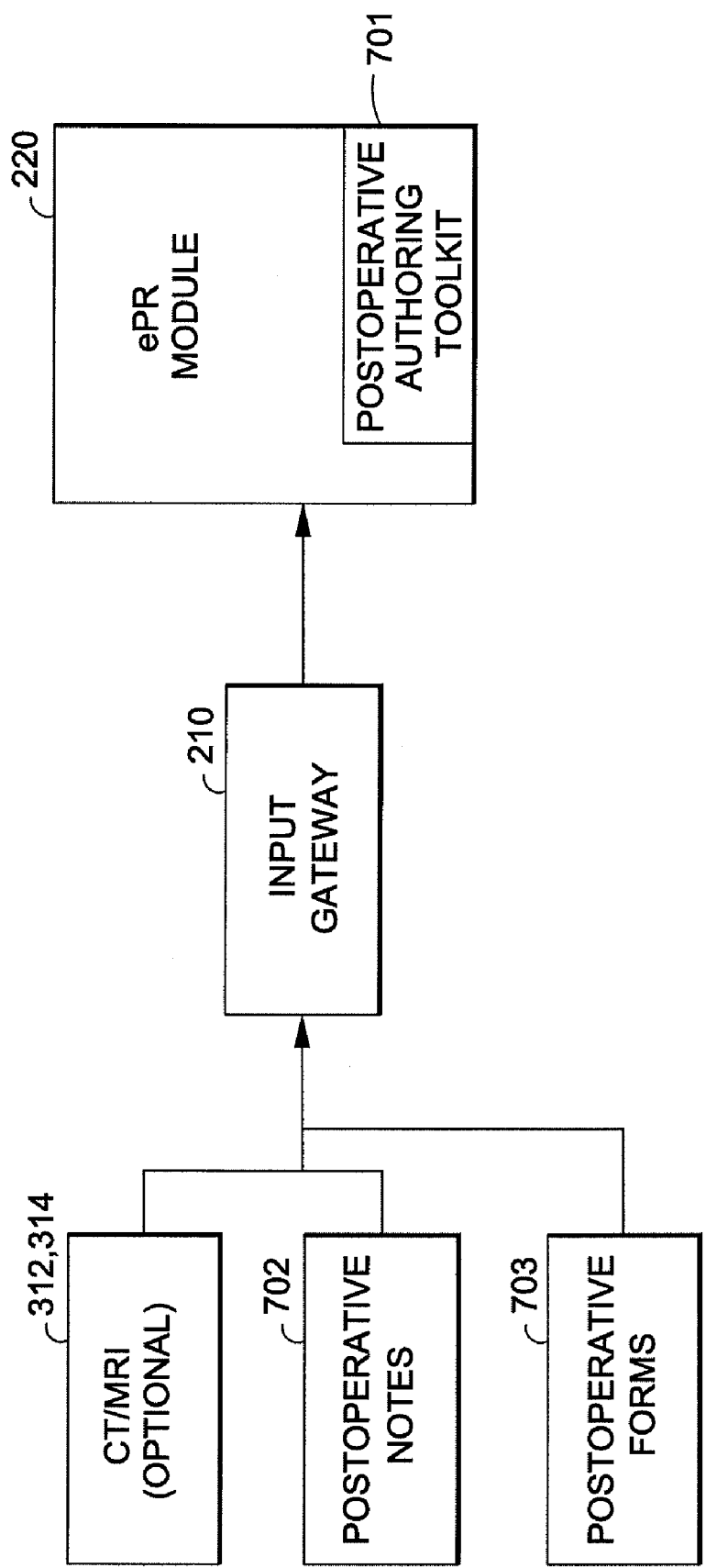
FIG. 7A illustrates a postoperative workflow according to one embodiment of the invention.

FIG. 7A illustrates a postoperative workflow according to one embodiment of the invention. Input gateway 210 receives postoperative notes 702, postoperative forms 703, and optionally CT data 314 and MRI data 312. Input gateway 210 may also receive C-arm images 134, endoscopic video 136, waveform data 302, patient evaluation data, and other intraoperative surgical video and data. Input gateway 210 transmits data to ePR module 220, which includes a postoperative authoring toolkit configured to create postoperative reports which may include text, sampled waveforms, and images.

Figure 7B:
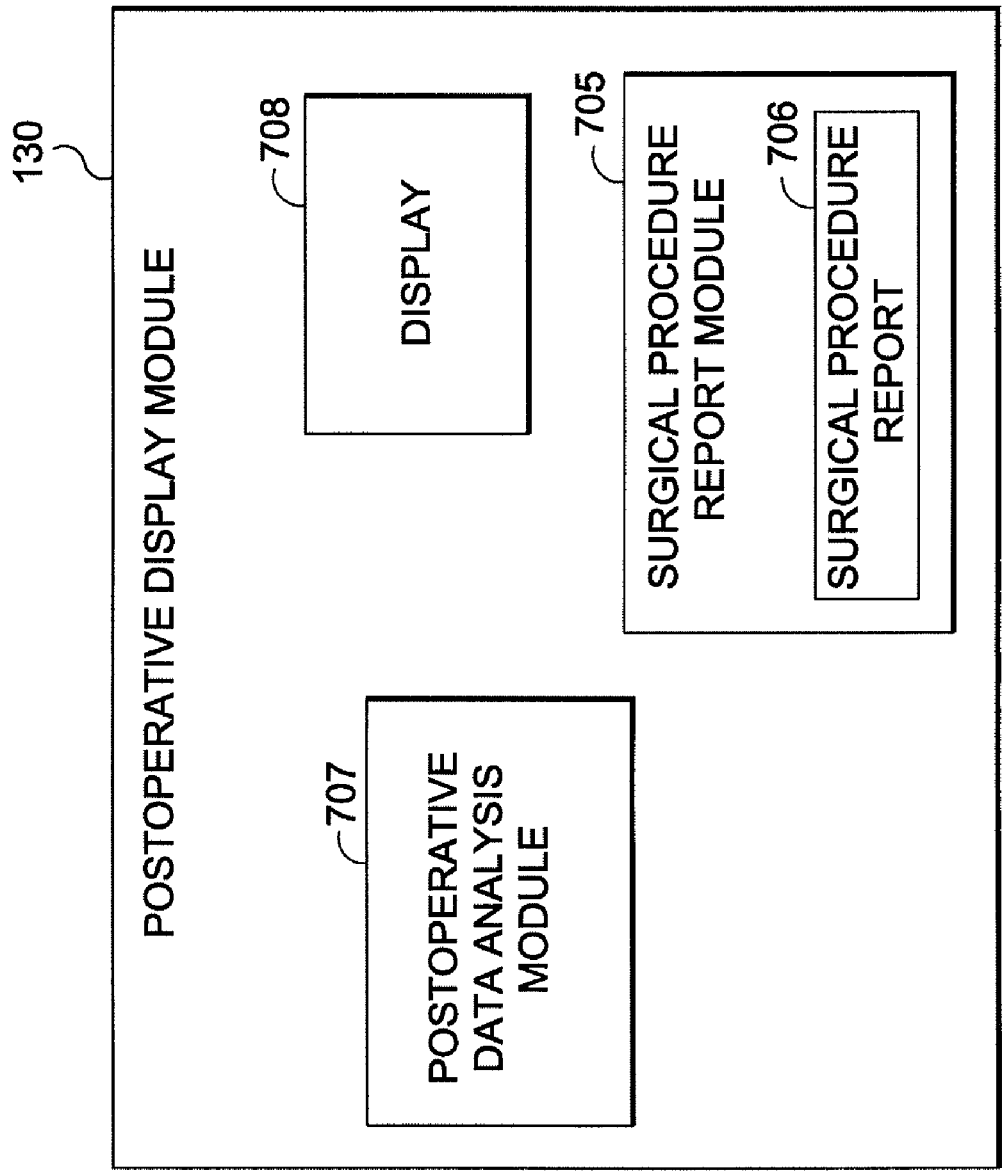
FIG. 7B illustrates a block diagram of the postoperative display module, including an authoring tool kit for generating a surgical procedure report, according to one embodiment of the invention.

FIG. 7B illustrates a block diagram of the postoperative display module 130, including an authoring tool kit for generating a surgical procedure report, according to one embodiment of the invention. In certain embodiments, the postoperative display module 130 consists of three systems: a postoperative data analysis module 707, a display and/or graphical user interface 708, and surgical procedure report information system 705. The data display 708 is configured to display any combination of preoperative data, intraoperative data, and postoperative data, such as, but not limited to, temperature, systolic pressure, diastolic pressure, heart rate, pulse oximeter, partial pressure of carbon dioxide, bispectral index (BIS) readings, respiratory rate, C-arm images, endoscopic images, preoperative key images, patient demographic data, pain forms, and endoscopic video clips. A BIS monitor is a neurophysiological monitoring device which continually analyses a patient's electroencephalograms during general anesthesia to assess the level of consciousness during anesthesia. Waveform and image data can be acquired automatically and/or simultaneously with or without a timestamp, and may also be displayed synchronously. The postoperative data analysis module 707 is configured to process any combination of preoperative data, intraoperative data, and postoperative data. In certain embodiments, surgical procedure report information system 705 is configured for the generation of surgical reports 706, such as by a surgeon, which may include patient information, key images selected from preoperative data, intraoperative data, and postoperative data. In certain embodiments, the output format can be portable document format or Microsoft Word format, while in other embodiments, other output formats may be used.

Figure 7C:
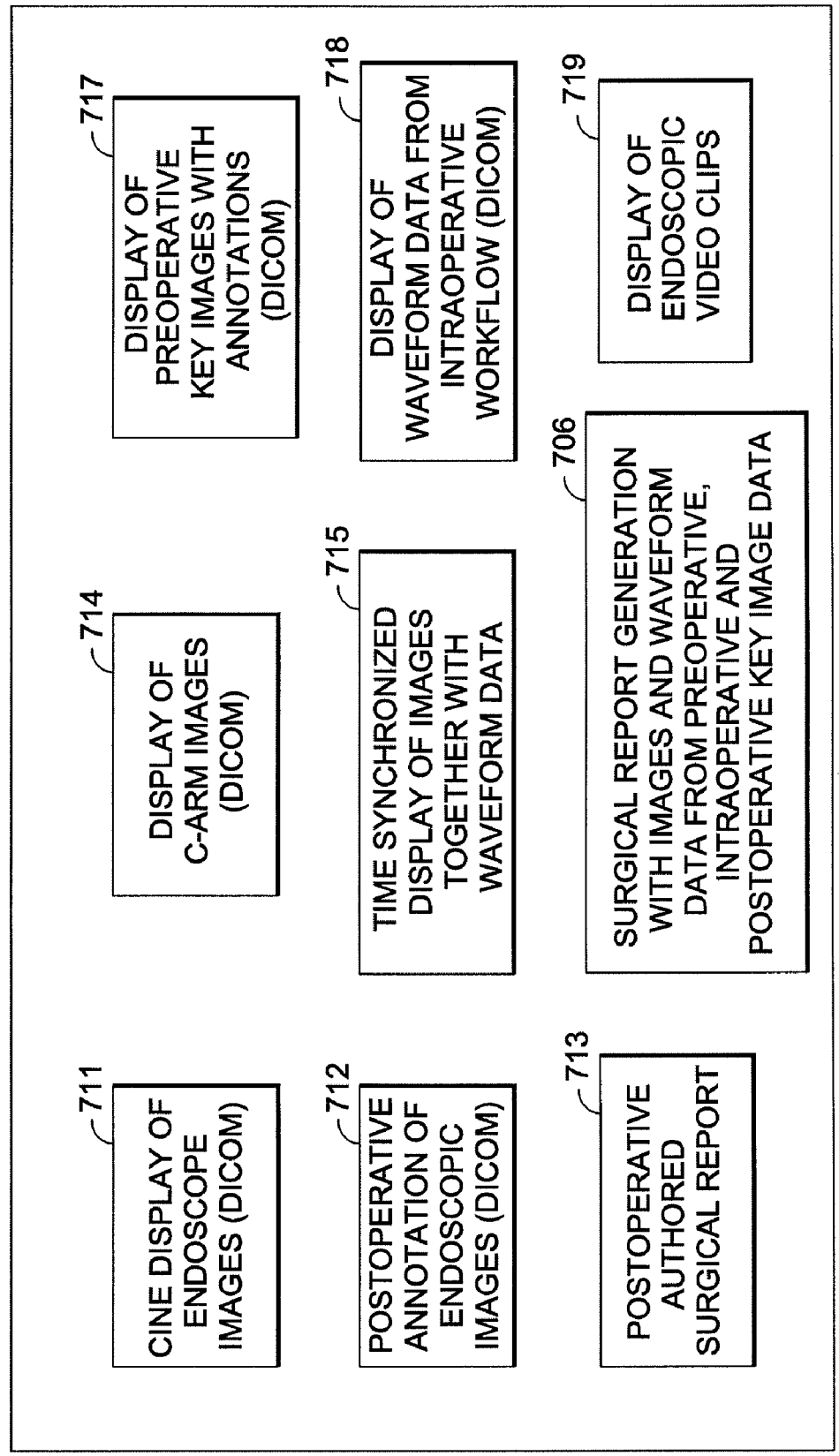
FIG. 7C illustrates a sample screenshot from a postoperative data display according to one embodiment of the invention.

FIG. 7C illustrates a sample screenshot from a postoperative data display 130 according to one embodiment of the invention. In certain embodiments, postoperative data display 130 displays data such as a cine display of endoscopic images 711, postoperative annotation of endoscopic images in DICOM format 712, postoperative authored surgical report 713, display of C-arm images in DICOM format 714, time synchronized display of images together with waveform data 715, a surgical procedure report 706 with images and waveform and key image data selected from preoperative data, intraoperative data, and postoperative data, display of preoperative key images with annotations in DICOM format 717, display of waveform data from an intraoperative workflow in DICOM format 718, and display of endoscopic video clips 719 which may, for example, be in MPEG format.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A surgical data monitoring and display system for use in an operating room or another patient care room, comprising:

a data storage module that stores retrospective data and real-time data concerning a patient;

a first processing module that receives the retrospective data, processes the retrospective data into processed retrospective data, and transmits the processed retrospective data to a first display module before or during performance of a medical or surgical procedure on the patient by a healthcare provider;

the first display module, which displays the processed retrospective data;

a first gateway that receives the retrospective data from a server and transmits the retrospective data to the data storage module;

a second processing module that receives the real-time data, processes the real-time data into processed real-time data, and transmits the processed real-time data to a second display module before or during performance of the medical or surgical procedure on the patient by the healthcare provider; and the second display module, which displays the processed real-time data;
wherein the real-time data concerning the patient comprises at least two of the following: electrocardiographic data, electroencephalographic data, pulse oximetry data, videoscopic data, and vital sign data;
wherein the retrospective data comprises at least one of imaging data, patient identification information, past medical history information, physical examination information, data concerning a past procedure performed on the patient, or data concerning another patient or a teaching case;
wherein the real-time data is acquired during performance of the medical or surgical procedure on the patient;
wherein the first display module and the second display module are positionable in the operating room or another patient care room such that they are viewable by the healthcare provider during the performance by the healthcare provider of the medical or surgical procedure on the patient;
a third processing module configured to receive postoperative data, the retrospective data, and the real-time data, and further configured to process at least one of the postoperative data, the retrospective data, or the real-time data into report data; and
a third display module, which displays the report data; and
an alert module, coupled to the second processing module and configured to provide, on a single display, a visible alert when a predetermined threshold of the real-time data is exceeded; wherein the visible alert comprises at least one of:
  moving displayed real-time data from a first location, less prominent on a display of the second display module to the healthcare provider, to a second location, more prominent on the display of the second display module to the healthcare provider while maintaining display of the processed retrospective data on the first display module to be visible to the health care provider; and
  enlarging a display of a first set of the processed real-time data, displayed at a first, smaller size on a display of the second display module, to a second, larger size on the display of the second display module while maintaining display of the processed retrospective data on the first display module to be visible to the health care provider;
wherein the first set of the processed real-time data comprises at least one of electrocardiographic data, electroencephalographic data, pulse oximetry data, videoscopic data, or vital sign data; and
wherein the display of the second display module further displays a second set of the processed real-time data adjacent to the display of the first set of the processed real-time data, the second set of the processed real-time data comprising at least one of electrocardiographic data, electroencephalographic data, pulse oximetry data, videoscopic data, or vital sign data.

2. The system of claim 1, wherein,
when the display of the first set of the processed real-time data is enlarged to the second, larger size on the display of the second display module, (i) the display of the first set of the processed real-time data overlaps the display of the second set of the processed real-time data, and/or (ii) the display of the second set of the processed real-time data is reduced in size.

3. The system of claim 1, wherein the visible alert further comprises changing a color of displayed real-time data on a display of the second display module.

4. The system of claim 1, wherein at least one of the first display module, the second display module, and or the third display module comprises a plasma display, liquid crystal display (LCD), nanocrystal display, three-dimensional (3D) display, cathode ray tube (CRT) display, light emitting diode (LED) display, nano-emissive display, or projection display.

5. The system of claim 1, further comprising an alert module, coupled to the second processing module and configured to provide a visible alert when a predetermined threshold of the real-time data is exceeded, wherein the visible alert comprises changing a color of displayed real-time data on a display of the second display module.

6. The system of claim 1, wherein the first gateway is configured to receive and transmit the retrospective data according to a predefined priority configuration.

7. The system of claim 1, wherein the first processing module and the second processing module comprise the same hardware or software processor.

8. The system of claim 1, wherein at least two of the first processing module, the second processing module, and third processing module provide fault tolerance for each other.

9. The system of claim 1, further comprising a fourth display module configured to provide fault tolerance for each of the first display module, the second display module, and third display module.

10. The system of claim 1, wherein the report data comprises a patient surgery record.

11. The system of claim 1, wherein the vital sign data comprises at least one of a heart rate, a respiratory rate, a blood pressure, and or a body temperature.

12. The system of claim 1, further comprising:
a second gateway that receives the real-time data from a server and transmits the real-time data to the data storage module; and
a third gateway that receives the postoperative data and transmits the postoperative data to the data storage module.

13. The system of claim 12, wherein each of the first gateway, the second gateway, and the third gateway provide fault tolerance for each other.

14. The system of claim 12, wherein the first gateway, the second gateway, and the third gateway constitute the same node on a computer network.

15. The system of claim 1, further comprising:
an imaging server;
wherein the first processing module receives the retrospective data from the imaging server; and
wherein the retrospective data comprises imaging data.

16. The system of claim 15, wherein the imaging server comprises a picture archiving and communications system (PACS) server.

17. The system of claim 1, wherein the real-time data further comprises at least one of electromyogram (EMG) data, imaging data, computed tomography (CT), magnetic resonance image (MRI) data, ultrasound data, C-Arm image data, fluoroscopy data, or X-Ray data.

18. A surgical data monitoring and display system for use in an operating room or another patient care room, comprising:
a data storage module that stores real-time data concerning a patient;
a first processing module that receives the real-time data, processes the real-time data into processed real-time data, and transmits the processed real-time data to a first display module before or during performance of a medical or surgical procedure on the patient by a healthcare provider; and the first display module, which displays the processed real-time data;

wherein the real-time data concerning the patient comprises at least two of the following: electrocardiographic data, electroencephalographic data, pulse oximetry data videoscopic data, and vital sign data;

wherein the real-time data is acquired during performance of the medical or surgical procedure on the patient; and wherein the first display module is positionable in the operating room or another patient care room such that they are viewable by the healthcare provider during the performance by the healthcare provider of the medical or surgical procedure on the patient;

a second processing module configured to receive postoperative data, retrospective data, and the real-time data, and further configured to process at least one of the postoperative data, the retrospective data, and or the real-time data into report data; and a second display module, which displays the report data;

an alert module, coupled to the first processing module and configured to provide, on a single display, a visible alert when a predetermined threshold of the real-time data is exceeded;

wherein the visible alert comprises at least one of:

moving displayed real-time data from a first location, less prominent on a display of the first display module to the healthcare provider, to a second location, more prominent on the display of the first display module to the healthcare provider while maintaining display of the report data on the second display module to be visible to the health care provider; and enlarging a display of a first set of the processed real-time data, displayed at a first, smaller size on a display of the first display module, to a second, larger size on the display of the first display module while maintaining display of the report data on the second display module to be visible to the health care provider;

wherein the first set of the processed real-time data comprises at least one of electrocardiographic data, electroencephalographic data, pulse oximetry data, videoscopic data, and or vital sign data;

wherein the display of the first display module further displays a second set of the processed real-time data adjacent to the display of the first set of the processed real-time data, the second set of the processed real-time data comprising at least one of electrocardiographic data, electroencephalographic data, pulse oximetry data, videoscopic data, and or vital sign data; and wherein when the display of the first set of the processed real-time data is enlarged to the second, larger size on the display of the first display module, (i) the display of the first set of the processed real-time data overlaps the display of the second set of the processed real-time data, and/or (ii) the display of the second set of the processed real-time data is reduced in size.

19. The system of claim 18, further comprising:

a third processing module that receives the retrospective data, processes the retrospective data into processed retrospective data, and transmits the processed retrospective data to a third display module before or during performance of the medical or surgical procedure on the patient by the healthcare provider;

the third display module, which displays the processed retrospective data; and a third gateway that receives the retrospective data from a server and transmits the retrospective data to the data storage module.

20. The system of claim 19, wherein at least one of the first display module, the second display module, or the third display module comprises a plasma display, liquid crystal display (LCD), nanocrystal display, three-dimensional (3D) display, cathode ray tube (CRT) display, light emitting diode (LED) display, nano-emissive display, and projection display.

21. The system of claim 19, wherein the third gateway is configured to receive and transmit the retrospective data according to a predefined priority configuration.

22. The system of claim 19, wherein the first processing module, the second processing module, and the third processing module comprise the same hardware or software processor.

23. The system of claim 19, wherein at least two of the first processing module, the second processing module, and third processing module provide fault tolerance for each other.

24. The system of claim 19, further comprising a fourth display module configured to provide fault tolerance for each of the first display module, the second display module, and third display module.

25. The system of claim 19, wherein the report data comprises a patient surgery record.

26. The system of claim 18, wherein the vital sign data comprises at least one of a heart rate, a respiratory rate, a blood pressure, or a body temperature.

27. The system of claim 19, further comprising:

a second gateway that receives the postoperative data and transmits the postoperative data to the data storage module; and a third gateway that receives the real-time data from a server and transmits the real-time data to the data storage module.

28. The system of claim 27, wherein each of the first gateway, the second gateway, and the third gateway provide fault tolerance for each other.

29. The system of claim 27, wherein the first gateway, the second gateway, and the third gateway constitute the same node on a computer network.

30. The system of claim 19, further comprising:

an imaging server;

wherein the third processing module receives the retrospective data from the imaging server; and wherein the retrospective data comprises imaging data.

31. The system of claim 30, wherein the imaging server comprises a picture archiving and communications system (PACS) server.

32. The system of claim 18, wherein the real-time data further comprises at least one of electromyogram (EMG) data, imaging data, computed tomography (CT), magnetic resonance image (MRI) data, ultrasound data, C-Arm image data, fluoroscopy data, or X-Ray data.

* * * * *